US008501417B2

(12) United States Patent
Pohlmann et al.

(10) Patent No.: US 8,501,417 B2
(45) Date of Patent: Aug. 6, 2013

(54) IMMUNOLOGICAL COMPOSITIONS AS CANCER BIOMARKERS AND/OR THERAPEUTICS

(75) Inventors: Paula R. Pohlmann, Nashville, TN (US); Ray Mernaugh, Nashville, TN (US); Carlos Arteaga, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 407 days.

(21) Appl. No.: 12/666,566

(22) PCT Filed: Jun. 26, 2008

(86) PCT No.: PCT/US2008/068291
§ 371 (c)(1),
(2), (4) Date: May 7, 2010

(87) PCT Pub. No.: WO2009/003082
PCT Pub. Date: Dec. 31, 2008

(65) Prior Publication Data
US 2010/0215647 A1    Aug. 26, 2010

Related U.S. Application Data

(60) Provisional application No. 60/946,295, filed on Jun. 26, 2007.

(51) Int. Cl.
*G01N 33/53* (2006.01)
*A61K 39/395* (2006.01)

(52) U.S. Cl.
USPC .................. 435/7.1; 424/131.1; 424/138.1

(58) Field of Classification Search
None
See application file for complete search history.

(56) References Cited

U.S. PATENT DOCUMENTS

| 6,984,494 B2 | 1/2006 | Ralph | 435/7.1 |
|---|---|---|---|
| 2002/0090662 A1 | 7/2002 | Ralph | 435/7.92 |
| 2002/0155527 A1 | 10/2002 | Stuart et al. | 435/69.1 |

FOREIGN PATENT DOCUMENTS

| EP | 1 544 215 | 6/2005 |
| WO | WO 97/22699 | 6/1997 |

OTHER PUBLICATIONS

Pohlmann et al (Breast Cancer Research and Treatment, 2006, 100, suppl 1, p. S41, IDS).*
Pohlmann et al (Breast Cancer Research and Treatment, Dec. 2006, vol. 1; Supplement 1; p. S41, abstract 1009, IDS).*
Ritter et al (Cancer Research, 2001, 61:6851-6859).*
Tosi et al (European J of Cancer, 1996, 32A:498-505).*
Crombet et al (J Clinical Oncology, 2004, 22:1646-1654).*
Baral et al (Int J Cancer 2001, 92:88-95).*
Pal et al (2003, Proc Am Assoc Cancer Research, 44:p. 170, abstract #860).*
Baral et al., "Murine monoclonal anti-idiotypic antibody as a surrogate antigen for human HER-2/neu," *Int. J. Cancer*, 92:88-95, 2001.
Bei et al., "Immune responses to all ErbB family receptors detectable in serum of cancer patients," *Oncogene*, 18:1267-1275, 1999.
Bhattacharya-Chatterjee et al., "Anti-idiotype antibody vaccine therapy for cancer," *Expert. Opin. Bio. Ther.*, 2:869-81, 2002.
Birebent et al., "Anti-idiotypic antibody and recombinant antigen vaccines in colorectal cancer patients," *Crit. Rev. Oncol. Hematol.*, 39:107-13, 2001.
Bradley et al., "Carcinogen-induced histone alteration in normal human mammary epithelial cells," *Carcinogenesis*, 28:2184-92, 2007.
Carter et al., "Humanization of an anti-p185HER2 antibody for human cancer therapy," *Proc. Natl. Acad. Sci. USA*, 89:4285-9, 1992.
Chakraborty et al., "Induction of human breast cancer-specific antibody responses in cynomolgus monkeys by a murine monoclonal anti-idiotype antibody," *Cancer Res.*, 55:152-530, 1995.
Chatterjee et al., "Diagnostic markers of ovarian cancer by high-throughput antigen cloning and detection on arrays," *Cancer Res.*, 66:1181-90, 2006.
Coelho et al., "Isolation and characterisation of a human anti-idiotypic scFv used as a surrogate tumour antigen to elicit an anti-HER-2/neu humoral response in mice," *Br. J. Cancer*, 90:2032, 41, 2004.
Corbet et al., "Allogeneic manipulation of the GAT idiotypic cascade. Immunization of C57BL/6 mice by BALB/c anti-idiotypes stimulates similar strain-specific V genes as the original antigen," *J. Immunol.*, 141:779-84, 1988.
Dawling et al., "Catechol-O-methyltransferase (COMT)-mediated metabolism of catechol estrogens: comparison of wild-type and variant COMT isoforms," *Cancer Res.*, 61:6716-22, 2001.
Díaz et al., "Immune responses in breast cancer patients immunized with an anti-idiotype antibody mimicking NeuGc-containing gangliosides," *Clin. Immunol.*, 107:80-9, 2003.
Disis et al., "Existent T-cell and antibody immunity to HER-2/neu protein in patients with breast cancer," *Cancer Res.*, 54:16-20, 1994.
Disis et al., "High-titer HER-2/neu protein-specific antibody can be detected in patients with early-stage breast cancer," *J. Clin. Oncol.*, 15:3363-3367, 1997.
Du et al., "Evidence that cytochrome P450 CYP2B19 is the major source of epoxyeicosatrienoic acids in mouse skin," *Arch. Biochem. Biophys.*, 435:125-33, 2005.
Dwyer et al., "Idiotypic network connectivity and a possible cause of myasthenia gravis," *J. Exp. Med.*, 164:1310-8, 1986.
Edl et al., "Assays for selection of single-chain fragment variable recombinant antibodies to metal nanoclusters," *Methods Mol. Biol.*, 303:113-20, 2005.

(Continued)

*Primary Examiner* — Laura B Goddard
(74) *Attorney, Agent, or Firm* — Parker Highlander PLLC

(57) ABSTRACT

The present invention concerns antibodies that react immunologically with anti-tumor antigen antibodies and compositions and methods related thereto. In particular, the antibodies that react immunologically with the anti-tumor antigen antibodies are employed in therapeutic, diagnostic, and prognostic embodiments related to cancer, including breast cancer, for example.

7 Claims, 29 Drawing Sheets

OTHER PUBLICATIONS

Erez-Alon et al., "Immunity to p53 induced by an idiotypic network of anti-p53 antibodies: generation of sequence-specific anti-DNA antibodies and protection from tumor metastasis," *Cancer Res.*, 58:5447-52, 1998.
Foon et al., "Antibody responses in melanoma patients immunized with an anti-idiotype antibody mimicking disialoganglioside GD2," *Clin. Cancer Res.*, 4:1117-24, 1998.
Hamanaka et al., "Circulating anti-MUC1 IgG antibodies as a favorable prognostic factor for pancreatic cancer," *Int. J. Cancer*, 103:97-100, 2003.
Hennig et al., "Heterogeneity among Helicobacter pylori strains in expression of the outer membrane protein BabA," *Infect. Immun.*, 72:3429-35, 2004.
Koda et al., "Application of tyramide signal amplification for detection of N-glycolylneuraminic acid in human hepatocellular carcinoma," *Int. J. Clin. Oncol.*, 8:317-21, 2003.
Lehmann et al., "Tumor-antigen-specific humoral immune response of animals to anti-idiotypic antibodies and comparative serological analysis of patients with small-cell lung carcinoma," *Int. J. Cancer*, 50:86-92, 1992.
López-Díaz de Cerio et al., "Anti-idiotype antibodies in cancer treatment," *Oncogene*, 26:3594-602, 2007.
Lutzky et al.,"Antibody-based vaccines for the treatment of melanoma," *Semin. Oncol.*, 29:462-70, 2002.
Maruyama et al., "Monoclonal anti-idiotypic antibody functionally mimics the human gastrointestinal carcinoma epitope GA733," *Int. J. Cancer*, 65:547-53, 1996.
McNeel et al., "Antibody immunity to prostate cancer associated antigens can be detected in the serum of patients with prostate cancer," *J. Urol.*, 164:1825-9, 2000.
Mernaugh et al., "Idiotype network components are involved in the murine immune response to simian virus 40 large tumor antigen," *Cancer Immunol. Immunother.*, 35:113-8, 1992.
Mernaugh et al., "Production and characterization of mouse ureteric bud cell-specific rat hybridoma antibodies utilizing subtractive immunization and high-throughput screening," *J. Immunol. Methods*, 306:115-27, 2005.
Mohanty et al., "Anti-tumor immunity induced by an anti-idiotype antibody mimicking human Her-2/neu," *Breast Cancer Res. Treat.*, 104:1-11, 2007.
Neeson et al., "Listeriolysin O is an improved protein carrier for lymphoma immunoglobulin idiotype and provides systemic protection against 38C13 lymphoma," *Cancer Immunol. Immunother.*, 57:493-505, 2007.
Pohl et al., "CD30-antigen-specific targeting and activation of T cells via murine bispecific monoclonal antibodies against CD3 and CD28: potential use for the treatment of Hodgkin's lymphoma," *Int. J. Cancer*, 54:418-25, 1993.
Pohlmann et al., "An active immune network is a surrogate marker for early tumor response to trastuzumab in a pre-clinical model of breast cancer," *Breast Cancer Research and Treatment*, 100:S41, 2006.
Presta et al., "Humanization of an anti-vascular endothelial growth factor monoclonal antibody for the therapy of solid tumors and other disorders," *Cancer Res.*, 57:4593-9, 1997.
Reff et al., "Depletion of B cells in vivo by a chimeric mouse human monoclonal antibody to CD20," *Blood*, 83:435-45, 1994.
Rifai et al., "Protein biomarker discovery and validation: the long and uncertain path to clinical utility," *Nat. Biotechnol.*, 24:971-83, 2006.
Ruiz et al., "Idiotypic immunization induces immunity to mutated p53 and tumor rejection," *Nat. Med.*, 4:710-2, 1998.
Shin et al., "Proapoptotic activity of cell-permeable anti-Akt single-chain antibodies," *Cancer Res.*, 65:2815-24, 2005.
Taylor et al., "Augmented HER-2 specific immunity during treatment with trastuzumab and chemotherapy," *Clin. Cancer Res.*, 13:5133-5143, 2007.
Tsujisaki et al., "Preparation and characterization of anti-anti-idiotypic monoclonal antibody ("Ab1-like Ab3") in relation to carcinoembryonic antigen," *J. Clin. Lab. Anal.*, 16:279-89, 2002.
Volanakis, "Human C-reactive protein: expression, structure, and function," *Mol. Immunol.*, 38:189-97, 2001.
von Mensdorff-Pouilly et al., "Survival in early breast cancer patients is favorably influenced by a natural humoral immune response to polymorphic epithelial mucin," *J. Clin. Oncol.*, 18:574-83, 2000.
Wikstrand et al., "Generation of anti-idiotypic reagents in the EGFRvIII tumor-associated antigen system," *Cancer Immunol. Immunother.*, 50:639-52, 2002.
Zhang et al., "Selection of active ScFv to G-protein-coupled receptor CCR5 using surface antigen-mimicking peptides," *Biochemistry*, 43:12575-84, 2004.

* cited by examiner

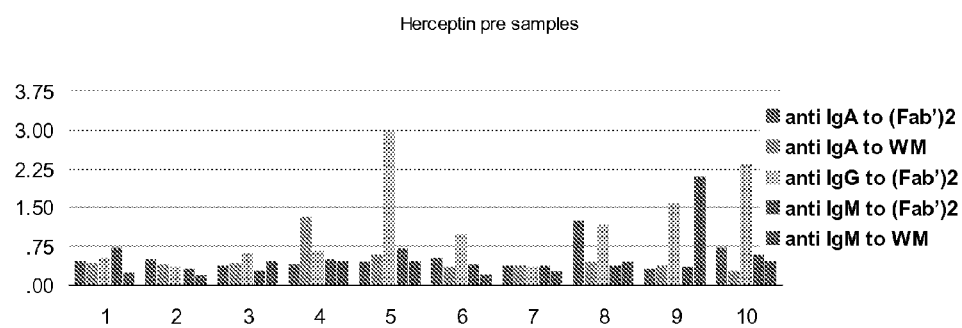
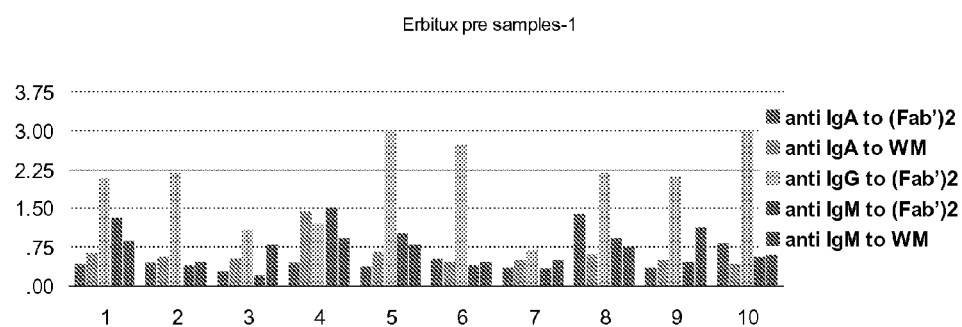
FIG. 18-2
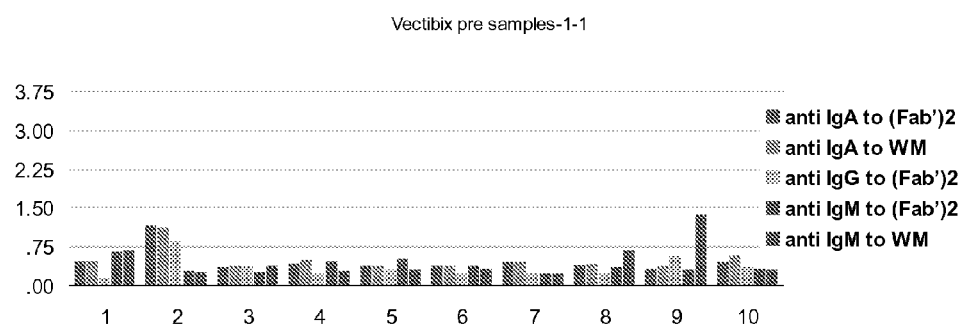
FIG. 18-3

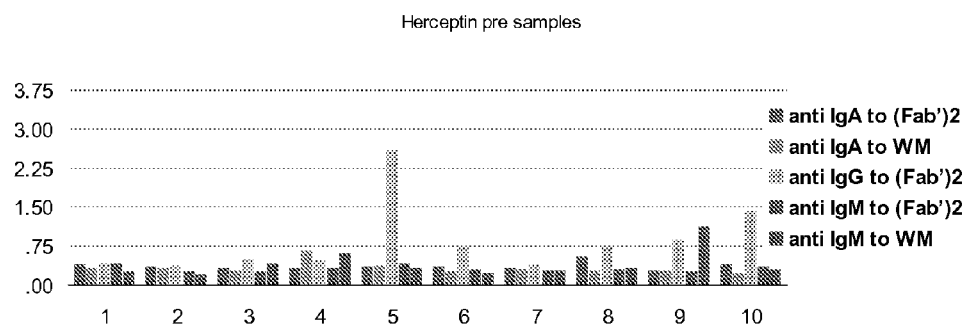
FIG. 20-2
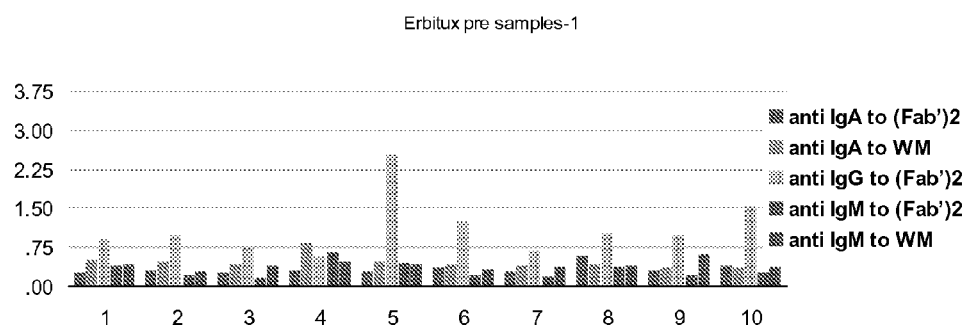
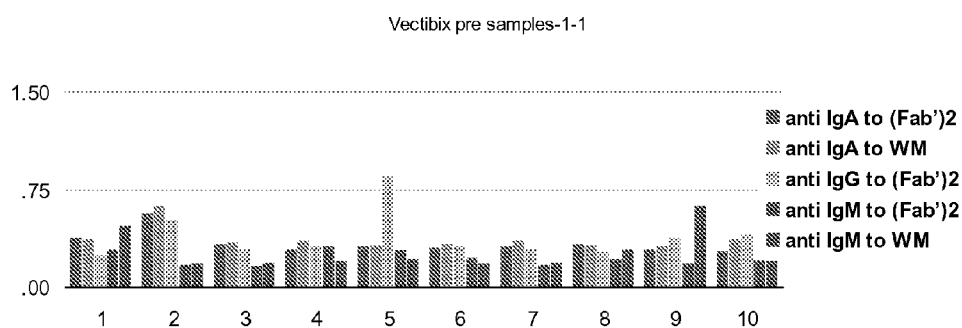
FIG. 20-3

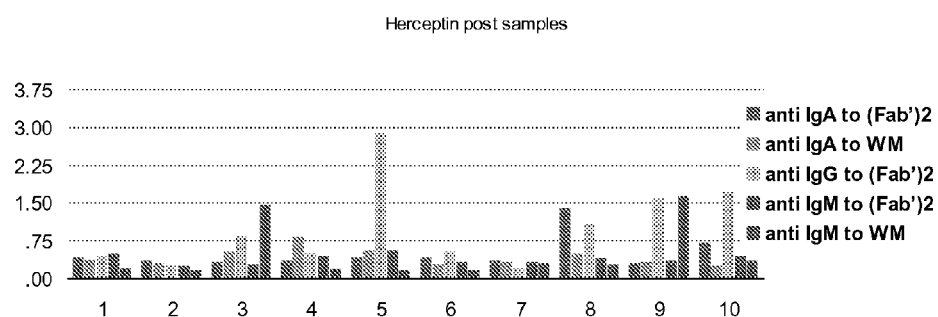
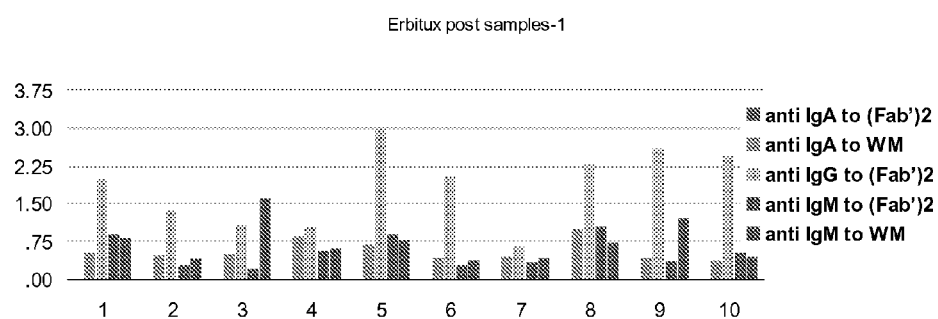
FIG. 22-2
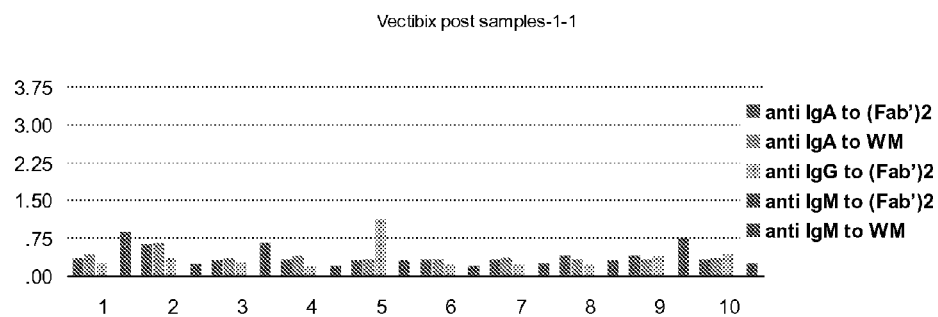
FIG. 22-3

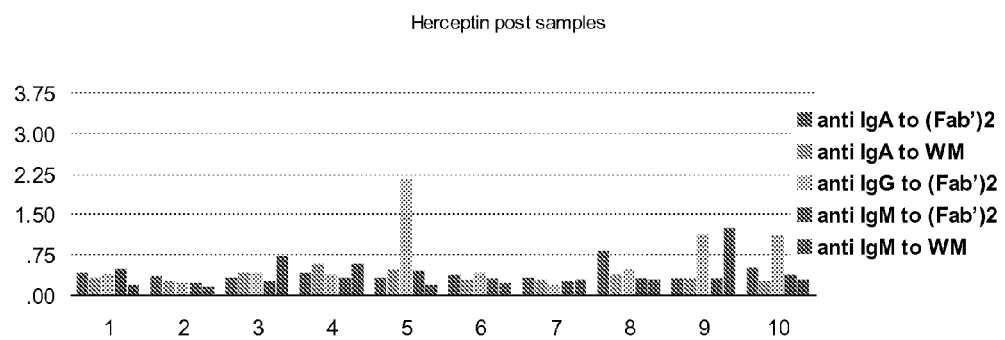
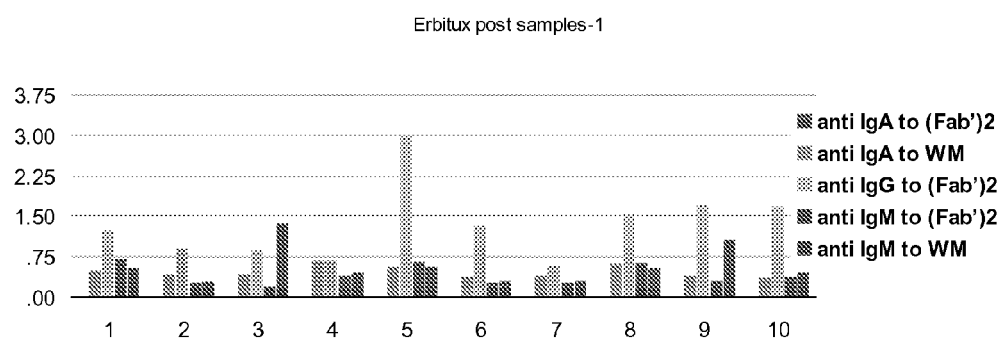
FIG. 23-2
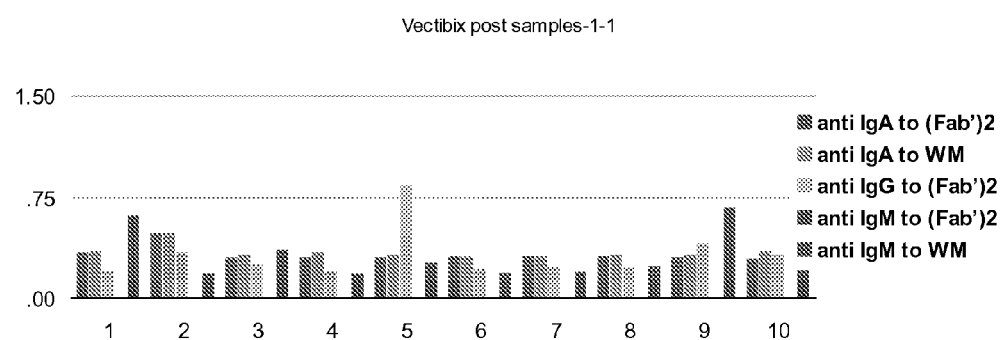
FIG. 23-3

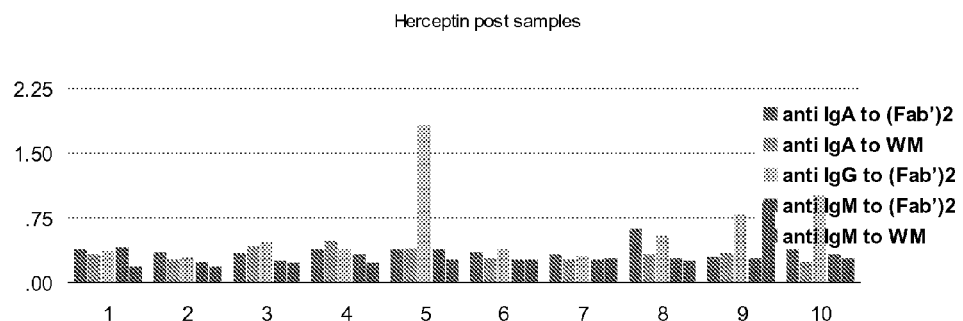
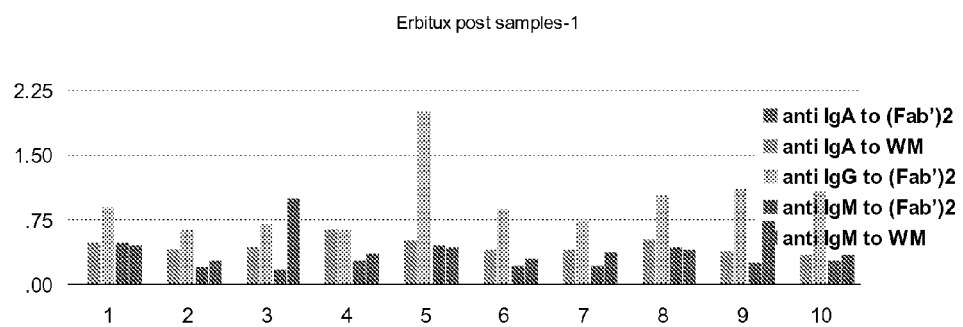
FIG. 24-2
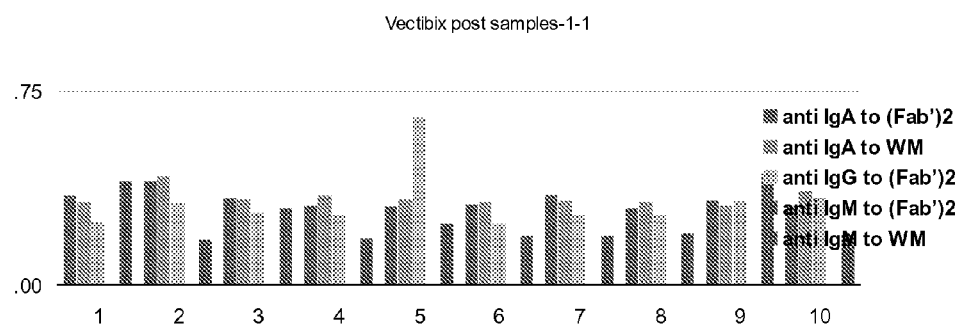
FIG. 24-3

IMMUNOLOGICAL COMPOSITIONS AS CANCER BIOMARKERS AND/OR THERAPEUTICS

PRIORITY CLAIM

This present application is a national phase application under 35 U.S.C. §371 of International Patent Application No. PCT/US2008/068291 filed Jun. 26, 2008 which claims priority to U.S. Provisional Application Ser. Nos. 60/946,295 filed Jun. 26, 2007, the entire contents of both applications being hereby incorporated by reference.

STATEMENT REGARDING FEDERALLY SPONSORED RESEARCH OR DEVELOPMENT

This invention was made with government support under Grant No. CA098131 awarded by the National Institutes of Health. The government has certain rights in the invention.

FIELD OF THE INVENTION

The present invention concerns at least the fields of cell biology, molecular biology, and cancer therapy, diagnosis, and prognosis. In particular, the present invention relates to methods and compositions regarding antibodies that bind antibodies directed to a tumor antigen.

BACKGROUND OF THE INVENTION

Approximately 50% of patients with ERBB2 (which may also be referred to as HER2) positive breast cancer develop cellular and humoral immune response to ERBB2 (Disis et al., 1994). Antibodies are directed both to ectodomains and to intracellular domains of ERBB2. Furthermore, both IgG and IgM anti-ERBB2 has been detected. Higher titers of endogenous Ab anti-ERBB2 ECD are present in earlier breast cancer clinical stages (Disis et al., 1997). In fact, spontaneous immune responses to all members of the ERBB family (EGFR, ERBB2, ERBB3, ERBB4) have been detected (Bei et al., 1999). Also, little is known about the effects of the endogenous antibodies on phosphorylation of ERBB2 and its downstream signaling. T cell proliferation assays also show reactivity to ERBB2 epitopes, but the meaning of this response is unknown as well.

According to the immune network hypothesis, if there is an immune response with antibody (Ab1) production, there will be a regulatory response, with production of another antibody (Ab2) directed to Ab1. Little is known about the presence of endogenous Ab directed to anti-HER2 Abs in subjects, or their potential impact on disease or treatments.

SUMMARY OF THE INVENTION

The present invention is directed to methods and compositions that concern immunological approaches to cancer treatment, diagnosis, and/or prognosis. In general, the present invention concerns antibodies that react immunologically with anti-tumor antigen antibodies, and methods and compositions related thereto for cancer treatment, diagnosis, and/or prognosis.

In particular, the invention relates to one or more biomarkers that can be used, such as in an antibody or protein array, for example, as a diagnostic tool to facilitate cancer diagnosis, for example by blood test, saliva, sputum and fibrobroncoscopy aspirate/washing (diagnosis for lung cancer, for example); and application including use of the Abs for immunohistochemistry or immunofluorescence in any biopsy, made by open procedure or by video, for example. The diagnostic test may detect early stage cancer, late stage cancer, or both. In other embodiments of the invention, there is a test, such as a blood test, that at least assists in selecting subjects for treatment with monoclonal antibodies. Furthermore, there is a new drug that increases cancer sensitivity to treatment with monoclonal antibodies e.g. trastuzumab, cetuximab, and so forth.

Specific but exemplary tumor antigens for which antibodies bind immunologically to antibodies to the tumor antigens comprise at least the following HER2, EGFR (HER1), HER3, HER4, VEGFR, CD20, or EpCAM. Specific but exemplary anti-tumor antigen antibodies include trastuzumab (Herceptin®), cetuximab (C225 or Erbitux®), rituximab (Rituxan® or Mabthera), Bevacizumab (Avastin®), Edrecolomab (Panorex®), panitumumab (Vectibix®) and Alemtuzumab (Campath®). The anti-tumor antigen antibodies may alternatively be endogenous to one or more subjects.

Antibodies that react immunogically with anti-tumor antigen antibodies (the anti-tumor antigen antibodies may be considered "therapeutic antibodies" and also may be considered Ab1) may be referred to as Ab2 and can also be employed in laboratories of research, such as to study binding affinity of tumors to therapeutic Abs (Ab1), in competition assays, for instance, or anytime during the development of anti-cancer Abs. In some cases, the antibody that reacts immunologically with the anti-tumor antigen antibody not only is an anti-idiotypic, but it can also work as an epibody, which is an antibody with an exquisite ability to bind to an idiotope and also directly to the antigen itself.

Therapeutic methods and compositions of the invention may be considered to be an initial therapy for cancer, it may be considered an adjuvant cancer therapy, or both. It can also be used as second, third, or any line of therapy for advanced or relapsed cancer. It could be used for cancer prevention, in certain embodiments.

Antibodies of the invention may be obtained commercially and/or generated by standard methods in the art, such as producing human mAb from circulating B-cells of a subject or by genetic engineering, for example.

Subjects for which the invention may be employed may be of any kind in need thereof. In specific examples, the cancer in the subjects may also be of any kind For example, the cancer may be HER2 positive, HER2 negative, EGFR positive, EGFR negative, and so forth. The cancer may be of any histology, or staging, as well there being embodiments to pre-malignant conditions.

Samples from the subject may be of any suitable kind, so long as they are amenable for assaying for antibodies therein. In specific embodiments, the samples comprise blood, plasma, serum, urine, nipple aspirate, saliva, sweat, cerebrospinal fluid, and so forth. Collection of the samples may be by any suitable method, although in some aspects collection is by needle, catheter, syringe, scrapings, and so forth.

Although in exemplary embodiments provided herein the invention is demonstrated with breast cancer aspects, the methods and compositions are applicable for any type of cancer. For example, the invention may be employed for lung, brain, prostate, colon, skin, pancreatic, cervical, head and neck, esophageal, throat, ovarian, testicular, bone, spleen, kidney, liver, gall bladder, thyroid, blood, and so forth.

In one embodiment of the invention, there is a method of diagnosing, predicting the development of, or staging cancer in a subject, comprising the step of detecting, in a sample from the subject, an antibody that reacts immunologically with an anti-tumor antigen antibody. In specific embodiments, the method may be further defined as detecting an anti-idiotypic antibody that reacts immunologically with the variable region of an anti-tumor antigen antibody.

In other embodiments of the invention, there is a method of determining a response of a subject to an anti-cancer treatment, wherein the treatment optionally comprises administration of an anti-tumor antigen antibody (or any other kind of cancer treatment, including conventional chemotherapy, targeted therapy, biologic response modifiers, hormonal therapy, as well as radiation therapy, surgery or other kinds of local therapy for tumors), the method comprising the step of detecting, in a sample from the subject, an antibody that reacts immunologically with the anti-tumor antigen antibody, wherein the presence of the antibody that reacts immunologically with the anti-tumor antigen antibody indicates that the subject will respond to the treatment. In alternative embodiments, the presence of the antibody that reacts immunologically with the anti-tumor antigen antibody indicates that the subject will not respond to the treatment. In specific embodiments, the method is further defined as detecting an anti-idiotypic antibody that reacts immunologically with the variable region of the anti-tumor antigen antibody, wherein the presence of the anti-idiotypic antibody indicates that the subject will respond to the treatment. In specific aspects, the subject has not received the treatment, although in other aspects, the subject has previously received the treatment. The treatment to which the determination of a response thereto is being made may be of any kind, including conventional chemotherapy, targeted therapy, biologic response modifiers, hormonal therapy, as well as radiation therapy, surgery or other kinds of local therapy for tumors, for example.

In an additional embodiment of the invention, there is a method of improving the treatment of a subject with cancer, wherein the treatment optionally comprises administration of an anti-tumor antigen antibody, comprising the step of delivering to the subject an antibody that reacts immunologically with an anti-tumor antigen antibody. In specific embodiments, the method is further defined as delivering to the subject an anti-idiotypic antibody that reacts immunologically with the variable region of an anti-tumor antigen antibody. In specific embodiments, the method further comprises treating the subject with an anti-tumor antigen antibody.

In an alternative embodiment, the anti-idiotypic antibody that reacts immunologically with the variable region of an anti-tumor antigen antibody is detrimental to a cancer therapy, such as by interfering with the activity of the anti-tumor antigen antibody. Thus, in specific embodiments an agent is delivered to a subject having an anti-idiotypic antibody that detrimentally reacts immunologically with the variable region of an anti-tumor antigen antibody. In particular, the agent prevents the interaction of the anti-tumor antigen antibody with the anti-idiotypic antibody that reacts immunologically with the variable region of the anti-tumor antigen antibody. In further specific embodiments, the agent is itself another antibody that is an anti-tumor antigen antibody. In other embodiments, the agent comprises a small molecule, protein, peptide, polypeptide, or nucleic acid.

In some embodiments, there is polyclonal antisera comprising antibodies that react immunologically with an anti-tumor antigen antibody, which may be further defined as comprising anti-idiotypic antibodies that react immunologically with the variable region of an anti-tumor antigen antibody. There are also monoclonal antibodies that react immunologically with an anti-tumor antigen antibody, which may be further defined as an antibody that reacts immunologically with the variable region of an anti-tumor antigen antibody. Hybridomas that produce the monoclonal antibodies are also contemplated.

In some embodiments of the invention, there is a composition, comprising: an antibody that reacts immunologically with an anti-tumor antigen antibody; and the anti-tumor antigen antibody. The composition may be further defined as comprising an anti-idiotypic antibody that reacts immunologically with the variable region of an anti-tumor antigen antibody; and the anti-tumor antigen antibody. The composition may be further defined as being comprised in a pharmaceutically acceptable excipient.

In another embodiment of the invention, there is a method of screening for an antibody that reacts immunologically with an anti-tumor antigen antibody, comprising (a) providing said anti-tumor antigen antibody; (b) contacting the anti-tumor antigen antibody with a test antibody; and (c) assessing binding of the test antibody to the anti-tumor antigen antibody. In specific embodiments, the method is further defined as a method of screening for an antibody that reacts immunologically with the variable region of an anti-tumor antigen antibody, comprising (a) providing said anti-tumor antigen antibody; (b) contacting the anti-tumor antigen antibody with a test antibody; and (c) assessing binding of said test antibody to the variable region of the anti-tumor antigen antibody. In specific aspects, the method further comprises the step of producing the test antibody. In additional specific embodiments, the producing step comprises immunizing an animal with the anti-tumor antigen antibody. In further specific embodiments, the method further comprises the step of preparing a hybridoma from B-cells of the animal.

In one embodiment of the invention, there is a method of determining a response to cancer treatment, wherein said treatment comprises an antibody that binds a tumor antigen on a cell of the individual, comprising the steps of obtaining a sample from the individual; and assaying the sample for one or more first antibodies that bind at least one second antibody, wherein said second antibody binds a tumor antigen on a cell of the individual. In a specific embodiment of the invention, when the sample from the individual comprises one or more first antibodies, said individual will respond to said treatment. In other specific embodiments, the second antibody is the treatment antibody. The method may occur prior to the cancer treatment or subsequent to initiation of the cancer treatment.

In another embodiment there is a method of treating an individual with cancer, comprising the step of delivering to the individual a first antibody that binds a second antibody, wherein said second antibody binds a tumor antigen on a cell of the individual. The second antibody may be endogenous to the individual and/or may be delivered to the individual.

In other embodiments, there is polyclonal antisera, wherein first antibodies of the antisera each recognize one or more second antibodies, wherein each of the second antibodies bind to a tumor antigen. Additional embodiments concern monoclonal antibodies that bind to a second antibody, wherein the second antibody binds to a tumor antigen. In further embodiments, there is a hybridoma that produces a monoclonal antibody of the invention.

Other embodiments of the invention include a composition, comprising a first antibody that binds to a second antibody, wherein the second antibody binds a tumor antigen; and the second antibody. The composition may be further defined as being comprised in a pharmaceutically acceptable excipient.

In further embodiments, there is a method of screening for a first antibody that binds a second antibody, wherein the second antibody binds to a tumor antigen, comprising the steps of providing the second antibody; and delivering to the second antibody a test antibody, wherein when the test antibody binds the second antibody, the test antibody is the first antibody. The method may further comprise the step of producing the first antibody, such as by producing the first antibody from a hybridoma. The method may also further comprise the step of delivering the first antibody to an individual that comprises the tumor antigen on a least one cell. The individual may be HER2-positive or HER2-negative. The method may further comprise the step of producing a recombinant single-chain variable antibody fragment, Fv, VL or VH fragment, a Fab idiotypic antibody fragment, or an anti-idiotypic antibody fragment from circulating B-cells of a patient or donor or by genetic engineering. Alternatively, the method may further comprise the step of producing a recombinant single-chain variable antibody fragment, Fv, VL or VH fragment, a Fab idiotypic antibody fragment, or an anti-idiotypic antibody fragment from phage-displayed, yeast or bacterial libraries obtained using lymphatic or circulating B-cells of a patient or donor or by genetic engineering.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

I. Definitions

Figure 1:
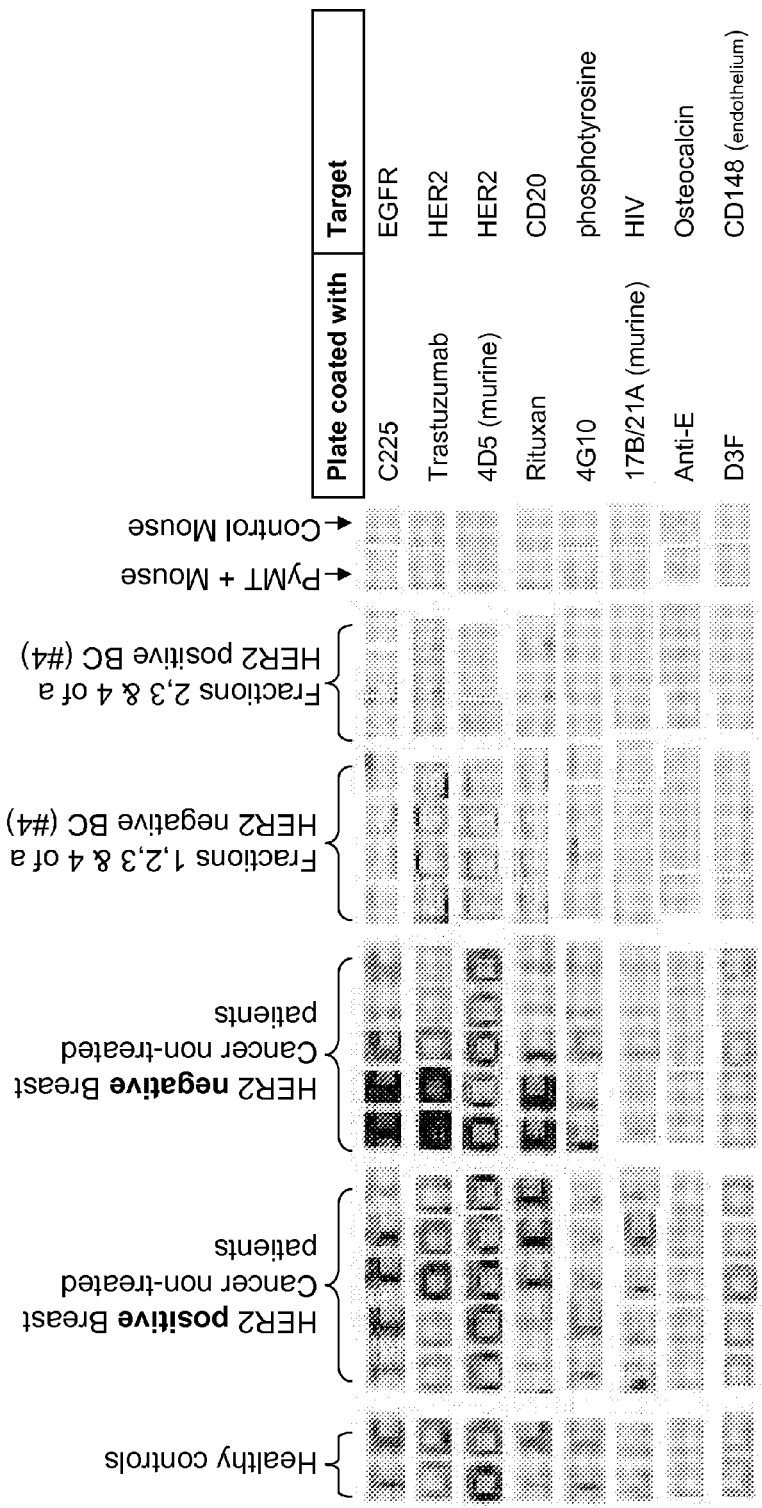
FIG. 1 demonstrates anti-human IgM/HRP.

As used herein the specification, "a" or "an" may mean one or more. As used herein in the claim(s), when used in conjunction with the word "comprising," the words "a" or "an" may mean one or more than one. As used herein "another" may mean at least a second or more. Some embodiments of the invention may consist of or consist essentially of one or more elements, method steps, and/or methods of the invention. It is contemplated that any method or composition described herein can be implemented with respect to any other method or composition described herein.

The term "antigen" or "immunogen" as used herein is defined as a molecule that provokes an immune response when it is introduced into a subject or produced by a subject (tumor antigens arise by the cancer development itself). This immune response may involve either antibody production, or the activation of specific immunologically-competent cells, or both. An antigen can be derived from organisms, subunits of proteins/antigens, killed or inactivated whole cells or lysates, although in the present invention the antigen is a tumor antigen on the surface of a cancer cell. Commonly, an antigen is a molecule that causes the subject in which it is introduced to produce antibodies that specifically recognize the antigen. The part of the antigen with which the antibody interacts is termed an "epitope" or "antigenic determinant". A skilled artisan realizes that any macromolecule, including virtually all proteins or peptides, can serve as antigens. Furthermore, antigens can be derived from recombinant or genomic DNA. A skilled artisan realizes that any DNA that contains nucleotide sequences or partial nucleotide sequences of a pathogenic genome or a gene or a fragment of a gene for a protein that elicits an immune response results in synthesis of an antigen.

The term "antigenic" and "immunogenic" as used herein describe a structure that is an antigen. These terms can be used interchangeably.

The term "antibody" as used herein refers to an immunoglobulin molecule, which is able to specifically bind to a specific epitope on an antigen. As used herein, an antibody is intended to refer broadly to any immunologic binding agent such as IgG, IgM, IgA, IgD and IgE. Antibodies can be intact immunoglobulins derived from natural sources or from recombinant sources and can be immunoactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)2, as well as single chain antibodies and humanized antibodies (Harlow et al., 1988; Bird et al., 1988).

As used herein, the term "pharmaceutically or pharmacologically acceptable" refers to molecular entities and compositions that do not produce adverse, allergic, or other untoward reactions when administered to an animal or a human.

The term "pharmaceutically acceptable carrier" or "pharmaceutically acceptable excipient" or "physiologically acceptable carrier" as used herein includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated. The carrier may not produce an adverse, allergic or other untoward reaction when administered to an animal, such as, for example, a human, as appropriate. These terms can be used interchangeably.

The term "subject" or "individual," as used herein refers to animals, including mammals. More specifically, mammals include, but are not limited to rats, mice, rabbits, cats, dogs, monkeys and humans. These terms can be used interchangeably.

II. Embodiments of the Present Invention

Human epidermal growth factor receptor-2 (HER2; also called ErbB2) is a cell-surface protein involved in cell development. Activation of HER2 in cancer cells accelerates many cellular processes associated with tumor formation, including cell proliferation, angiogenesis, adhesion, and resistance to chemotherapy. About 25% of breast cancers overexpress HER2, which is found on their cell surface. Trastuzumab (see, for example, U.S. Pat. No. 6,800,738) is a therapeutic monoclonal Ab that targets tumor cells that overexpress HER2 and is used to treat HER2-positive breast cancer. In patients previously treated with cytotoxic chemotherapy whose tumors overexpress HER2, administration of Trastuzumab as a single agent results in a response rate of 25%.

Immunity against HER2 is present in about 30-50% of patients with HER2-positive breast cancer. According to Jerne's immune network hypothesis, if there is an immune response with antibody (Ab1) production, there may be a regulatory response, with production of a second antibody (Ab2) that binds to and interacts with Ab1. Little is known about the presence of endogenous antibody (Ab) directed to therapeutic anti-HER2 Abs in patients or in animals.

The present inventors have detected endogenous anti-anti-HER2 Abs (Ab2) in the serum of untreated patients suffering from HER2-positive and HER2-negative breast cancer, but rarely in healthy donors. Additionally, in a breast cancer murine model, the presence of anti-anti-HER2 or anti-anti-EGFR endogenous antibodies in the serum of mice was directly related to better tumor response to standard immunotherapeutic treatment.

Therefore, it is contemplated that endogenous antibodies (e.g., Ab2), present in humans, that interact with therapeutic anti-HER2 (e.g., Herceptin/Trastuzumab) or anti-EGFR (e.g. Erbitux/Cetuximab) antibodies may be useful in one or more different settings: (1) biomarkers for cancer diagnosis; (2) biomarkers for cancer prognosis; (3) biomarker for treatment selection in personalized medicine; and/or (4) therapy when used individually, or in combination with standard therapy for cancer.

In certain aspects of the invention, hybridomas are generated that produce the anti-anti-HER2 and anti-anti-EGFR antibodies in the laboratory. With higher amounts of purified antibodies, one will be able to proceed with steps to further characterize settings 1-4 above. In additional embodiments these Abs are characterized as follows: (1) to characterize their anti-tumor effect using in vitro systems; (2) to describe Ab sequence; (3) to characterize the target-epitopes for the Abs; and/or (4) to further develop diagnostic and/or therapeutic embodiments of the invention.

III. Antibodies for Immunotherapy

The present invention provides antibodies to be used as immunotherapy for hyperproliferative diseases and disorders. The antibodies of the present invention are immunogically reactive with anti-tumor antigen antibodies and are compatible with the human immune system. Thus, in one aspect, the invention is directed to a humanized monoclonal antibody immunoreactive with anti-tumor antigen antibodies wherein the framework regions (FRs) of the variable regions of said antibody and the constant regions of said antibody are compatible with the human immune system. More specifically, the monoclonal antibody or immunoreactive fragment thereof, is immunoreactive with anti-tumor antigen antibodies and compatible with the human immune system, wherein the framework regions (FRs) of the variable regions of said antibody or fragment and any constant regions of said antibody or fragment are of human origin.

Thus, as used herein the term "humanized" is directed to antibodies or fragments immunospecific for anti-tumor antigen antibodies that have sufficient human characteristics so that their immunogenicity in human systems is lowered with respect to the corresponding antibodies derived from other species. Thus, the humanized antibodies or immunoreactive fragments of the invention are compatible with the human immune system. By "compatible with the human immune system" is meant that the antibodies or fragments of the invention do not elicit a substantial immune response when administered to humans as compared to unmodified forms of nonhuman antibodies containing the same complementarity-determining regions (CDRs). Eliciting an immune response is clearly undesirable as antibodies raised against therapeutically administered materials undermine the effectiveness of the administered materials and in addition may provoke unwanted side-effects due to stimulation of the immune system per se. While the antibodies and fragments of the invention may not, of course, be completely neutral with respect to an immune response in a specific individual, their effect on the immune system of an individual will be substantially less than that elicited by corresponding nonhuman antibodies in their unmodified forms.

Yet further, as used herein, the term "fully human antibody" or "fully humanized antibody" refers to antibodies or fragments immunospecific for human anti-tumor antigen antibodies that have relatively no CDR or FR residues substituted from analogous sites in nonhuman species. Thus, the human variable domain is intact.

As discussed herein, minor variations in the amino acid sequences of antibodies or immunoglobulin molecules are contemplated as being encompassed by the humanized antibodies of the present invention, providing that the variations in the amino acid sequence maintain at least 75%, more preferably at least 80%, 90%, 95%, and most preferably 99% homology to the human variable domain. Specifically, in the present invention if the humanized antibody maintains at least 95% and most preferably 99% homology to the human variable domain, then the humanized antibody is considered to be fully humanized.

In particular, the variations that may be contemplated are conservative amino acid replacements. Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=lysine, asparagine, glutamine, cysteine, serine, threonine, tyrosine. More particular families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Fragments or analogs of antibodies or immunoglobulin molecules can be readily prepared by those of ordinary skill in the art. Particular amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known (Bowie et al., 1991).

Particular amino acid substitutions are those such as follows: (1) reduce susceptibility to proteolysis, (2) reduce susceptibility to oxidation, (3) alter binding affinity for forming protein complexes, (4) alter binding affinities, and (4) confer or modify other physiocochemical or functional properties of such analogs. Analogs can include various mutations of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence).

IV. Antibody Preparation

Yet further, the antibodies of the present invention that react immunologically with anti-tumor antigen antibodies may be produced using standard procedures that are well known and used in the art.

A. Polyclonal Antibodies

Polyclonal antibodies that react immunologically to anti-tumor antigen antibodies generally are raised in animals by multiple subcutaneous (sc) or intraperitoneal (ip) injections of the anti-tumor antigen antibodies and an adjuvant.

Animals are immunized against the immunogenic composition or derivatives. Animals are boosted until the titer plateaus. The animals are usually bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography.

B. Monoclonal Antibodies

The methods for generating monoclonal antibodies (MAbs) generally begin along the same lines as those for preparing polyclonal antibodies. Rodents such as mice and rats are particular animals, however, the use of rabbit, sheep, goat, monkey cells also is possible. The use of rats may provide certain advantages (Goding, 1986), but mice are used, with the BALB/c mouse being most routinely used and generally gives a higher percentage of stable fusions.

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies. Methods for generating monoclonal antibodies are described elsewhere herein.

C. Humanized Antibodies

Methods for humanizing non-human antibodies are well known in the art. Generally, a humanized antibody has one or more amino acid residues introduced into it from a source, which is non-human. These non-human amino acid residues are often referred to as "import" residues, which are typically taken from an "import" variable domain. Humanization can be essentially performed following the method of Winter and co-workers (Jones et al., 1986; Riechmann et al., 1988; Verhoeyen et al., 1988), by substituting rodent CDRs or CDR sequences for the corresponding sequences of a human antibody. Accordingly, such "humanized" antibodies are chimeric antibodies wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It may be beneficial that antibodies be humanized with retention of high affinity for the antigen and other favorable biological properties. To achieve this goal, according to a particular method, humanized antibodies are prepared by a process of analysis of the parental sequences and various conceptual humanized products using three-dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen.

D. Human Antibodies

Human monoclonal antibodies can be made by the hybridoma method. Human myeloma and mouse-human heteromyeloma cell lines for the production of human monoclonal antibodies have been described (Kozbor, 1984; U.S. Pat. No. 6,150,584, which is incorporated herein by reference).

It is now possible to produce transgenic animals (e.g., mice) that are capable, upon immunization, of producing a repertoire of human antibodies in the absence of endogenous immunoglobulin production. For example, it has been described that the homozygous deletion of the antibody heavy chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. (Jakobovits et al., 1993).

Alternatively, the phage display technology (McCafferty et al., 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle.

V. Immunotherapy Treatments

A. Treatment of Hyperproliferative Diseases

In certain embodiments, a hyperproliferative disease may be treated by administering to a subject an effective amount of antibodies that react immunologically with anti-tumor antigen antibodies. The subject is preferably a mammal and more preferably a human. In alternative embodiments, a hyperproliferative disease may be treated by administering to a subject an effective amount of an agent that inhibits the immunological reaction between an antibody that reacts immunologically with an anti-tumor antigen antibody and the anti-tumor antigen antibody itself.

In the present invention, a hyperproliferative disease is further defined as cancer. In still further embodiments, the cancer is melanoma, non-small cell lung, small-cell lung, lung, leukemia, hepatocarcinoma, retinoblastoma, astrocytoma, glioblastoma, gum, tongue, neuroblastoma, head, neck, breast, pancreatic, prostate, renal, bone, testicular, ovarian, mesothelioma, cervical, gastrointestinal, lymphoma, brain, colon, sarcoma or bladder.

The cancer may include a tumor comprised of tumor cells. For example, tumor cells may include, but are not limited to melanoma cell, a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, or a soft tissue cancer cell.

In a particular embodiment of the present invention, antibodies that react immunologically to anti-tumor antigen antibodies are administered in an effective amount to decrease, reduce, inhibit or abrogate the growth of cancer, including of a solid tumor. Examples of solid tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Yet further, hyperproliferative diseases that are most likely to be treated in the present invention are those that metastasize. It is understood by those in the art that metastasis is the spread of cells from a primary tumor to a noncontiguous site, usually via the bloodstream or lymphatics, which results in the establishment of a secondary tumor growth. Examples of hyperproliferative diseases contemplated for treatment include, but are not limited to melanoma, bladder, non-small cell lung, small cell lung, lung, hepatocarcinoma, retinoblastoma, astrocytoma, glioblastoma, neuroblastoma, head, neck, breast, pancreatic, gum, tongue, prostate, renal, bone, testicular, ovarian, mesothelioma, cervical, gastrointestinal lymphoma, brain, or colon cancer and any other hyperproliferative diseases that may be treated by administering an antibody that reacts immunologically with an anti-tumor antigen antibody.

B. Treatment Regimens

Treatment regimens may vary as well, and often depend on tumor type, tumor location, disease progression, and health and age of the patient. Obviously, certain types of tumor will require more aggressive treatment, while at the same time, certain patients cannot tolerate more taxing protocols. The clinician will be best suited to make such decisions based on the known efficacy and toxicity (if any) of the therapeutic formulations.

In certain aspects, patients to be treated will have adequate bone marrow function (defined as a peripheral absolute granulocyte count of >2,000/mm$^3$ and a platelet count of 100,000/mm$^3$), adequate liver function (bilirubin<1.5 mg/dl) and adequate renal function (creatinine<1.5 mg/dl).

As used herein the term "effective amount" is defined as an amount of the agent that will decrease, reduce, inhibit or otherwise abrogate the growth of a cancer cell, induce apoptosis, inhibit angiogenesis of a tumor cell, inhibit metastasis, or induce cytotoxicity in cells. Thus, an effective amount is an amount sufficient to detectably and repeatedly ameliorate, reduce, minimize or limit the extent of the disease or its symptoms. More rigorous definitions may apply, including elimination, eradication or cure of disease.

To kill cells, inhibit cell growth, inhibit metastasis, decrease tumor or tissue size and otherwise reverse or reduce the malignant phenotype of tumor cells, using the methods and compositions of the present invention, one would generally contact anti-tumor antigen antibodies with an antibody that reacts immunologically thereto. The routes of administration will vary, naturally, with the location and nature of the lesion, and include, e.g., intradermal, transdermal, parenteral, intravenous, intramuscular, intranasal, subcutaneous, percutaneous, intratracheal, intraperitoneal, intratumoral, perfusion, lavage, direct injection, and oral administration and formulation.

In the case of surgical intervention, the present invention may be used preoperatively, to render an inoperable tumor subject to resection. Alternatively, the present invention may be used at the time of surgery, and/or thereafter, to treat residual or metastatic disease. For example, a resected tumor bed may be injected or perfused with a formulation comprising an antibody that reacts immunologically with an anti-tumor antigen antibody. The perfusion may be continued post-resection, for example, by leaving a catheter implanted at the site of the surgery. Periodic post-surgical treatment also is envisioned.

Continuous administration also may be applied where appropriate, for example, where a tumor is excised and the tumor bed is treated to eliminate residual, microscopic disease. Delivery via syringe or catherization is in particular contemplated. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs. It is further contemplated that limb perfusion may be used to administer therapeutic compositions of the present invention, particularly in the treatment of melanomas and sarcomas.

In certain embodiments, the tumor being treated may not, at least initially, be resectable. Treatments with therapeutic antibodies may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

A typical course of treatment, for a primary tumor or a post-excision tumor bed, will involve multiple doses. Typical primary tumor treatment involves a 6 dose application over a two-week period. The two-week regimen may be repeated one, two, three, four, five, six or more times. During a course of treatment, the need to complete the planned dosings may be re-evaluated.

The treatments may include various "unit doses." Unit dose is defined as containing a predetermined-quantity of the therapeutic composition. The quantity to be administered, and the particular route and formulation, are within the skill of those in the clinical arts. A unit dose need not be administered as a single injection but may comprise continuous infusion over a set period of time.

C. Treatment regimen for breast cancer

It is envisioned that breast cancer, as only an exemplary cancer for treatment with the present invention, may be treated by employing the antibody treatment of the present invention. For example, antibodies that react immunologically to anti-tumor antigen antibodies may be employed at a starting dose of 1-3 mg/kg. Dosing may be every 3 weeks for 4 cycles (total=12 weeks), at which time response may also be determined. If no dose-limiting toxicity is observed after 2 cycles, then the next dosing level may be initiated according to standard dose-escalation algorithms (i.e., 3 mg/kg, 6 mg/kg, 9 mg/kg, 13.5 mg/kg, etc.).

In addition to toxicity and response data, tissue and serum samples are collected pre-therapy and post-therapy (after 2 and 4 cycles) to provide the basis for studies on intermediate biomarkers involved in angiogenesis and invasion and to evaluate whether these markers can predict response to treatment. To assess for alterations in blood flow, in situ, blood flow patterns are assessed in real time using 3D re-constructions of high resolution cutaneous Doppler ultrasound examinations of accessible tumors pre-therapy and after 2 to 4 cycles.

VI. Combination Treatments

In some embodiments of the invention, it may be desirable to combine compositions for administration to the subject, particularly combining antibodies that react immunologically with anti-tumor antigen antibodies and the anti-tumor antigen antibodies themselves. Yet further, it may be desirable to combine either antibodies that react immunologically with anti-tumor antigen antibodies and/or the anti-tumor antigen antibodies themselves with other agents effective in the treatment of hyperproliferative disease, such as anti-cancer agents, or with surgery. It is also contemplated that both antibodies that react immunologically with anti-tumor antigen antibodies with the anti-tumor antigen antibodies themselves may be administered in combination with an additional anti-cancer agent. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. Anti-cancer agents include biological agents (biotherapy), chemotherapy agents, and radiotherapy agents. More generally, these other compositions would be provided in a combined amount effective to kill or inhibit proliferation of the cell. This process may involve contacting the cells with the antibodies of the present invention and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the antibodies and the other includes the second agent(s).

In some embodiments, the antibodies that react immunologically with the anti-tumor antigen antibody or the anti-tumor antigen antibody itself react additively or synergistically with each other, or an another agent acts additively or synergistically with one or more of the antibodies that react immunologically with the anti-tumor antigen antibody or the anti-tumor antigen antibody itself.

Alternatively, the antibodies of the present invention (antibodies that react immunologically with anti-tumor antigen antibodies and the anti-tumor antigen antibodies themselves) may precede or follow the other anti-cancer agent treatment by intervals ranging from minutes to weeks. In embodiments where the other anti-cancer agent and antibodies are applied separately to the cell, one would generally ensure that a significant period of time did not expire between the time of each delivery, such that the agent and antibodies would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, antibodies is "A" and the secondary agent, such as radio- or chemotherapy, is "B", or antibodies that react immunologically with anti-tumor antigen antibodies is "A" and the anti-tumor antigen antibodies themselves are "B":

```
A/B/A    B/A/B  B/B/A   A/A/B    A/B/B B/A/A   A/B/B/B B/A/B/B
B/B/B/A  B/B/A/B         A/A/B/B A/B/A/B        A/B/B/A B/B/A/A
B/A/B/A  B/A/A/B         A/A/A/B B/A/A/A        A/B/A/A A/A/B/A
```

Administration of the immunotherapy of the present invention to a patient will follow general protocols for the administration of chemotherapeutics. It is expected that the treatment cycles would be repeated as necessary. It also is contemplated that various standard therapies, as well as surgical intervention, may be applied in combination with the described hyperproliferative cell therapy.

A. Chemotherapy

Cancer therapies also include a variety of chemical based treatments. Some examples of chemotherapeutic agents include antibiotic chemotherapeutics such as Doxorubicin, Daunorubicin, Adriamycin, Mitomycin (also known as mutamycin and/or mitomycin-C), Actinomycin D (Dactinomycin), Bleomycin, Plicomycin, plant alkaloids such as Taxol, Vincristine, Vinblastine, miscellaneous agents such as Cisplatin (CDDP), etoposide (VP16), Tumor Necrosis Factor, and alkylating agents such as, Carmustine, Melphalan (also known as alkeran, L-phenylalanine mustard, phenylalanine mustard, L-PAM, or L-sarcolysin, is a phenylalanine derivative of nitrogen mustard), Cyclophosphamide, Chlorambucil, Busulfan (also known as myleran), and Lomustine.

Some examples of other agents include, but are not limited to, Carboplatin, Procarbazine, Mechlorethamine, Camptothecin, Ifosfamide, Nitrosurea, Etoposide (VP16), Tamoxifen, Raloxifene, Toremifene, Idoxifene, Droloxifene, TAT-59, Zindoxifene, Trioxifene, ICI 182,780, EM-800, Estrogen Receptor Binding Agents, Gemcitabien, Navelbine, Farnesyl-protein transferase inhibitors, Transplatinum, 5-Fluorouracil, hydrogen peroxide, and Methotrexate, Temazolomide (an aqueous form of DTIC), Mylotarg, Dolastatin-10, Bryostatin, or any analog or derivative variant of the foregoing.

B. Radiotherapeutic Agents

Radiotherapeutic agents and factors include radiation and waves that induce DNA damage for example, γ-irradiation, X-rays, UV-irradiation, microwaves, electronic emissions, radioisotopes, and the like. Therapy may be achieved by irradiating the localized tumor site with the above described forms of radiations. It is most likely that all of these factors effect a broad range of damage DNA, on the precursors of DNA, the replication and repair of DNA, and the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

C. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

D. Gene Therapy

In yet another embodiment, gene therapy in conjunction with the combination therapy using the antibody compounds described in the invention are contemplated. A variety of proteins are encompassed within the invention, some of which are described below. Various genes that may be targeted for gene therapy of some form in combination with the present invention are known in the art, including p53, BRCA1, and/or BRCA2, for example.

VII. Immunological Reagents

In certain aspects of the invention, one or more antibodies are employed for either therapeutic, prognostic, and/or diagnostic embodiments. Antibodies include any type of antibody, and specifically refer to antibodies that react immunologically with anti-tumor antigen antibodies and/or anti-tumor antigens, in certain embodiments. In particular, these antibodies may be used in various diagnostic or therapeutic applications, described herein below.

As used herein, the term "antibody" is intended to refer broadly to any immunologic binding agent such as IgG, IgM, IgA, IgD and IgE. The term "antibody" is used to refer to any antibody-like molecule that has an antigen binding region, and includes antibody fragments such as Fab', Fab, F(ab')2, single domain antibodies (DABs), Fv, scFv (single chain Fv), and the like. The techniques for preparing and using various antibody-based constructs and fragments are well known in the art. Means for preparing and characterizing antibodies are also well known in the art (see, e.g., Antibodies: A Laboratory Manual, Cold Spring Harbor Laboratory, 1988; incorporated herein by reference).

Monoclonal antibodies (MAbs) are recognized to have certain advantages, e.g., reproducibility and large-scale production. The invention thus provides monoclonal antibodies of the human, murine, monkey, rat, hamster, rabbit and even chicken origin. Due to the ease of preparation and ready availability of reagents, murine monoclonal antibodies will often be utilized.

However, "humanized" antibodies are also contemplated, as are chimeric antibodies from mouse, rat, or other species, bearing human constant and/or variable region domains, bispecific antibodies, recombinant and engineered antibodies and fragments thereof. Methods for the development of antibodies that are "custom-tailored" to the patient's dental disease are likewise known and such custom-tailored antibodies are also contemplated.

The methods for generating monoclonal antibodies (MAbs) generally begin along the same lines as those for preparing polyclonal antibodies. Briefly, a polyclonal antibody is prepared by immunizing an animal with a LEE or CEE composition in accordance with the present invention and collecting antisera from that immunized animal.

A wide range of animal species can be used for the production of antisera. Typically the animal used for production of antisera is a rabbit, a mouse, a rat, a hamster, a guinea pig or a goat. The choice of animal may be decided upon the ease of manipulation, costs or the desired amount of sera, as would be known to one of skill in the art.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, chemokines, cofactors, toxins, plasmodia, synthetic compositions or LEEs or CEEs encoding such adjuvants.

Adjuvants that may be used include IL-1, IL-2, IL-4, IL-7, IL-12, γ-interferon, GM-CSF, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary adjuvants include complete Freund's adjuvant (a non-specific stimulator of the immune response containing killed Mycobacterium tuberculosis), incomplete Freund's adjuvants and aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, Pa.); low-dose Cyclophosphamide (CYP; 300 mg/m2) (Johnson/Mead, N.J.), cytokines such as γ-interferon, IL-2, or IL-12 or genes encoding proteins involved in immune helper functions, such as B-7.

The amount of immunogen composition used in the production of polyclonal antibodies varies upon the nature of the immunogen as well as the animal used for immunization. A variety of routes can be used to administer the immunogen including but not limited to subcutaneous, intramuscular, intradermal, intraepidermal, intravenous and intraperitoneal. The production of polyclonal antibodies may be monitored by sampling blood of the immunized animal at various points following immunization.

A second, booster dose (e.g., provided in an injection), may also be given. The process of boosting and titering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography.

MAbs may be readily prepared through use of well-known techniques, such as those exemplified in U.S. Pat. No. 4,196, 265, incorporated herein by reference. Typically, this technique involves immunizing a suitable animal with a selected immunogen composition, e.g., a purified or partially purified protein, polypeptide, peptide or domain, be it a wild-type or mutant composition. The immunizing composition is administered in a manner effective to stimulate antibody producing cells. In some embodiments, however, the antibody that reacts immunologically with the anti-tumor antigen antibody and/or the anti-tumor antigen antibody are present endogenously in a subject.

The methods for generating monoclonal antibodies (MAbs) generally begin along the same lines as those for preparing polyclonal antibodies. Rodents such as mice and rats are often used, however, the use of rabbit, sheep or frog cells is also possible.

The animals are injected with antigen, generally as described above. The antigen may be mixed with adjuvant, such as Freund's complete or incomplete adjuvant. Booster administrations with the same antigen or DNA encoding the antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible.

Often, a panel of animals will have been immunized and the spleen of an animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody producing B lymphocytes from the immunized animal are then fused with cells of an immortal myeloma cell, generally one of the same species as the animal that was immunized. Myeloma cell lines suited for use in hybridoma producing fusion procedures preferably are non antibody producing, have high fusion efficiency, and enzyme deficiencies that render then incapable of growing in certain selective media which support the growth of only the desired fused cells (hybridomas).

[Any one of a number of myeloma cells may be used, as are known to those of skill in the art (Goding, pp. 65-66, 1986;

Campbell, pp. 75-83, 1984). For example, where the immunized animal is a mouse, one may use P3 X63/Ag8, X63 Ag8.653, NS1/1.Ag 4 1, Sp2/0 Ag14, FO, NSO/U, MPC 11, MPC11 X45 GTG 1.7 and S194/5XX0 Bul; for rats, one may use R210.RCY3, Y3 Ag 1.2.3, IR983F and 4B210; and U 266, GM1500 GRG2, LICR LON HMy2 and UC729 6 are all useful in connection with human cell fusions.

One particular murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8 azaguanine resistant mouse murine myeloma SP2/0 non producer cell line.

Methods for generating hybrids of antibody producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al., (1977). The use of electrically induced fusion methods is also appropriate (Goding pp. 71-74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The favored selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody producing cell lines, which clones can then be propagated indefinitely to provide MAbs. The cell lines may be exploited for MAb production in two basic ways. First, a sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. Second, the individual cell lines could be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It is also contemplated that a molecular cloning approach may be used to generate monoclonals. In one embodiment, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies. In another example, LEEs or CEEs can be used to produce antigens in vitro with a cell free system. These can be used as targets for scanning single chain antibody libraries. This would enable many different antibodies to be identified very quickly without the use of animals.

Alternatively, monoclonal antibody fragments encompassed by the present invention can be synthesized using an automated peptide synthesizer, or by expression of full-length gene or of gene fragments in E. coli.

A. Antibody Conjugates

The present invention further provides antibodies to ORF transcribed messages and translated proteins, polypeptides and peptides, generally of the monoclonal type, that are linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radio-labeled nucleotides, antiviral agents, chelating agents, cytokines, growth factors, and oligo- or poly-nucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Any antibody of sufficient selectivity, specificity or affinity may be employed as the basis for an antibody conjugate. Such properties may be evaluated using conventional immunological screening methodology known to those of skill in the art.

Sites for binding to biological active molecules in the antibody molecule, in addition to the canonical antigen binding sites, include sites that reside in the variable domain that can bind pathogens, B-cell superantigens, the T cell co-receptor CD4 and the HIV-1 envelope (Sasso et al., 1989; Shorki et al., 1991; Silvermann et al., 1995; Cleary et al., 1994; Lenert et al., 1990; Berberian et al., 1993; Kreier et al., 1991). In addition, the variable domain is involved in antibody self-binding (Kang et al., 1988), and contains epitopes (idiotopes) recognized by anti-antibodies (Kohler et al., 1989).

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired. Another such example is the formation of a conjugate comprising an antibody linked to a cytotoxic or anti cellular agent, and may be termed "immunotoxins".

Antibody conjugates are used as diagnostic agents. Antibody diagnostics generally fall within two classes, those for use in in vitro diagnostics, such as in a variety of immunoassays, and/or those for use in vivo diagnostic protocols, generally known as "antibody directed imaging".

Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III). Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being commonly used in certain embodiments, and technicium99m and/or indium$^{111}$ are also often used due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938, 948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987).

This approach has been reported to produce diagnostically and therapeutically promising antibodies which are currently in clinical evaluation.

B. Immunodetection Methods

In still further embodiments, the present invention concerns immunodetection methods for binding, purifying, removing, quantifying and/or otherwise generally detecting biological components such as antibodies that react immunologically with anti-tumor antigen antibodies and/or the anti-tumor antigen antibodies themselves. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle and Ben-Zeev, 1999; Gulbis and Galand, 1993; De Jager et al., 1993; and Nakamura et al., 1987, each incorporated herein by reference.

In general, the immunobinding methods include obtaining a sample suspected of containing antibodies that react immunologically with anti-tumor antigen antibodies, and contacting the sample with a first anti-antibodies that react immunologically with anti-tumor antigen antibodies antibody in accordance with the present invention, as the case may be, under conditions effective to allow the formation of immunocomplexes.

These methods include methods for purifying an antibody that reacts immunologically with anti-tumor antigen antibodies from organelle, cell, tissue or organism's samples. In these instances, the antibody removes the antigenic antibodies that react immunologically with anti-tumor antigen antibodies message, protein, polypeptide and/or peptide component from a sample. The antibody will preferably be linked to a solid support, such as in the form of a column matrix, and the sample suspected of containing the antibodies that react immunologically with anti-tumor antigen antibodies component will be applied to the immobilized antibody. The unwanted components will be washed from the column, leaving the antigen immunocomplexed to the immobilized antibody to be eluted.

The immunobinding methods also include methods for detecting and quantifying the amount of an antigen component in a sample and the detection and quantification of any immune complexes formed during the binding process. Here, one would obtain a sample suspected of containing an antigen, and contact the sample with an antibody against the antibodies that react immunologically with anti-tumor antigen antibodies produced antigen, and then detect and quantify the amount of immune complexes formed under the specific conditions.

In terms of antigen detection, the biological sample analyzed may be any sample that is suspected of containing an antigen, such as, for example, a tissue section or specimen, a homogenized tissue extract, a cell, an organelle, separated and/or purified forms of any of the above antigen-containing compositions, or even any biological fluid that comes into contact with the cell or tissue, including blood and/or serum, although tissue samples or extracts may be used.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antibodies that react immunologically with anti-tumor antigen antibodies present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

The immunodetection methods of the present invention have evident utility in the diagnosis and prognosis of conditions such as cancer wherein a specific tumor antigen is expressed, and wherein antibodies exist that react immunologically to an anti-tumor antigen antibody Here, a biological and/or clinical sample suspected of containing a specific disease associated antibody is used. However, these embodiments also have applications to non-clinical samples, such as in the titering of antigen or antibody samples, for example in the selection of hybridomas.

In the clinical diagnosis and/or monitoring of patients with various forms a disease, such as, for example, cancer, the detection of a cancer specific antibodies that react immunologically with anti-tumor antigen antibodies, and/or an alteration in the levels of antibodies that react immunologically with anti-tumor antigen antibodies, in comparison to the levels in a corresponding biological sample from a normal subject is indicative of a patient with cancer. However, as is known to those of skill in the art, such a clinical diagnosis would not necessarily be made on the basis of this method in isolation. Those of skill in the art are very familiar with differentiating between significant differences in types and/or amounts of biomarkers, which represent a positive identification, and/or low level and/or background changes of biomarkers. Indeed, background expression levels are often used to form a "cut-off" above which increased detection will be scored as significant and/or positive. Of course, the antibodies of the present invention in any immunodetection or therapy known to one of ordinary skill in the art.

1. ELISAs

As detailed above, immunoassays, in their most simple and/or direct sense, are binding assays. Certain immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

In some aspects of the invention, there are ELISA/trastuzumab assays, including in kits, to test samples of subjects that are starting treatment with trastuzumab, to predict response. This may be considered is a new use for a known Ab. In addition, there may be an ELISA/therapeutic Abs kit, to test all at once. In particular, exemplary mAbs that concern the invention include trastuzuman (Herceptin®), cetuximab, (C225 or Erbitux®), rituximab (Rituxan® or Mabthera), Bevacizumab (Avastin®), Edrecolomab (Panorex®), and Alemtuzumab (Campath®).

In one exemplary ELISA, the anti-ORF message and/or anti-ORF translated product antibodies of the invention are immobilized onto a selected surface exhibiting protein affinity, such as a well in a polystyrene microtiter plate. Then, a test composition suspected of containing the antigen, such as a clinical sample, is added to the wells. After binding and/or washing to remove non-specifically bound immune complexes, the bound antigen may be detected. Detection is generally achieved by the addition of another anti-ORF message and/or anti-ORF translated product antibody that is linked to a detectable label. This type of ELISA is a simple "sandwich ELISA". Detection may also be achieved by the addition of a second anti-ORF message and/or anti-ORF translated product antibody, followed by the addition of a third antibody that has binding affinity for the second antibody, with the third antibody being linked to a detectable label.

In another exemplary ELISA, the samples suspected of containing the antigen are immobilized onto the well surface and/or then contacted with the anti-ORF message and/or anti-ORF translated product antibodies of the invention. After binding and/or washing to remove non-specifically bound immune complexes, the bound anti-ORF message and/or anti-ORF translated product antibodies are detected. Where the initial anti-ORF message and/or anti-ORF translated product antibodies are linked to a detectable label, the immune complexes may be detected directly. Again, the immune complexes may be detected using a second antibody that has binding affinity for the first anti-ORF message and/or anti-ORF translated product antibody, with the second antibody being linked to a detectable label.

Another ELISA in which the antigens are immobilized, involves the use of antibody competition in the detection. In this ELISA, labeled antibodies against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A particular washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

2. Immunohistochemistry

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in 70° C. isopentane; cutting the plastic capsule and/or removing the frozen cylinder of tissue; securing the tissue cylinder on a cryostat microtome chuck; and/or cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

VIII. Pharmaceutical Formulations and Delivery

The pharmaceutical or antibody compositions disclosed herein may be administered parenterally, intravenously, intradermally, intramuscularly, transdermally or even intraperitoneally as described in U.S. Pat. No. 5,543,158; U.S. Pat. No. 5,641,515 and U.S. Pat. No. 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, specific methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

IX. Kits of the Invention

Any of the compositions of the invention may be comprised in a kit. The kit may comprise a suitably aliquoted antibody that reacts immunologically with an anti-tumor antigen antibody and the anti-tumor antigen antibody, wash solutions, blocking agents, reporter molecules, means for detecting the reporter molecule, a suitable solid surface support means such as a microplate and/or additional reagents. The components of the kits may be packaged either in aqueous media or in lyophilized form. When reagents and/or components are provided as a dry powder, the powder can be reconstituted by the addition of a suitable solvent. It is envisioned that the solvent may also be provided. Additionally, a microplate or other suitable solid surface support means may be provided pre-bound to one or more antibody that reacts immunologically with an anti-tumor antigen antibody or the anti-tumor antigen antibody.

The container means of the kits will generally include at least one vial, test tube, flask, bottle, syringe or other container means, into which a component may be placed, and preferably, suitably aliquoted. Where there is more than one component in the kit, the kit also will generally contain a second, third or other additional containers into which the additional components may be separately placed. However, various combinations of components may be comprised in a vial. The kits of the present invention also will typically include a means for containing the reagent vials and other kit components in close confinement for commercial sale. Such containers may include injection or blow molded plastic containers into which the desired vials are retained.

In specific embodiments, the kit comprises an ELISA assay with any antibodies that react immunologically with anti-tumor antigen antibodies and/or anti-tumor antigen antibodies.

Irrespective of the number or type of containers, the kits of the invention may also comprise, or be packaged with, an instrument for assisting with the injection/administration or placement of the immunogenic composition within the body of an animal. Such an instrument may be a syringe, pipette, forceps, or any such medically approved delivery vehicle.

X. Examples

The following examples are included to demonstrate particular embodiments of the invention. It should be appreciated by those of skill in the art that the techniques disclosed in the examples which follow represent techniques discovered by the inventors to function well in the practice of the invention, and thus can be considered to constitute particular modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Presence of Immune Network Related to Cancer Immunity

In early studies by the inventors, human serum IgM antibodies bound to the anti-tumor antigen antibodies C225 (anti-EGFR-antibody also referred to as cetuximab) and trastuzumab immobilized on the bottom of a plate. The present inventors provide a more extensive characterization in this Example.

Ab1 coated 384 well plates, and the exemplary test antibodies, trastuzumab and C225, whereas exemplary control antibodies included murine 4D5 and 17B/21A and rituximab, anti-E, 4G10, and D3F. Serum samples were added to the wells, including test samples having 5 HER2+ untreated early stage breast cancer patients and having 5 HER2-untreated early stage breast cancer patients. Control samples included two healthy donors and mouse samples. Plates were washed, and anti-human IgG or IgM labeled antibodies.

FIG. 1 demonstrates anti-human IgM/horse radish peroxidase (HRP). This study confirmed the previous study. Human serum Abs (Ab2) bound to C225 (Ab1) and trastuzumab (Ab1) immobilized on the bottom of a plate, and not to control antibodies. HER2 and 4D5 plates were slightly different. Ab2 class tested was IgM, and Ab2 is also present in the serum of HER2 positive and HER2 negative breast cancer patients.

Figure 2:
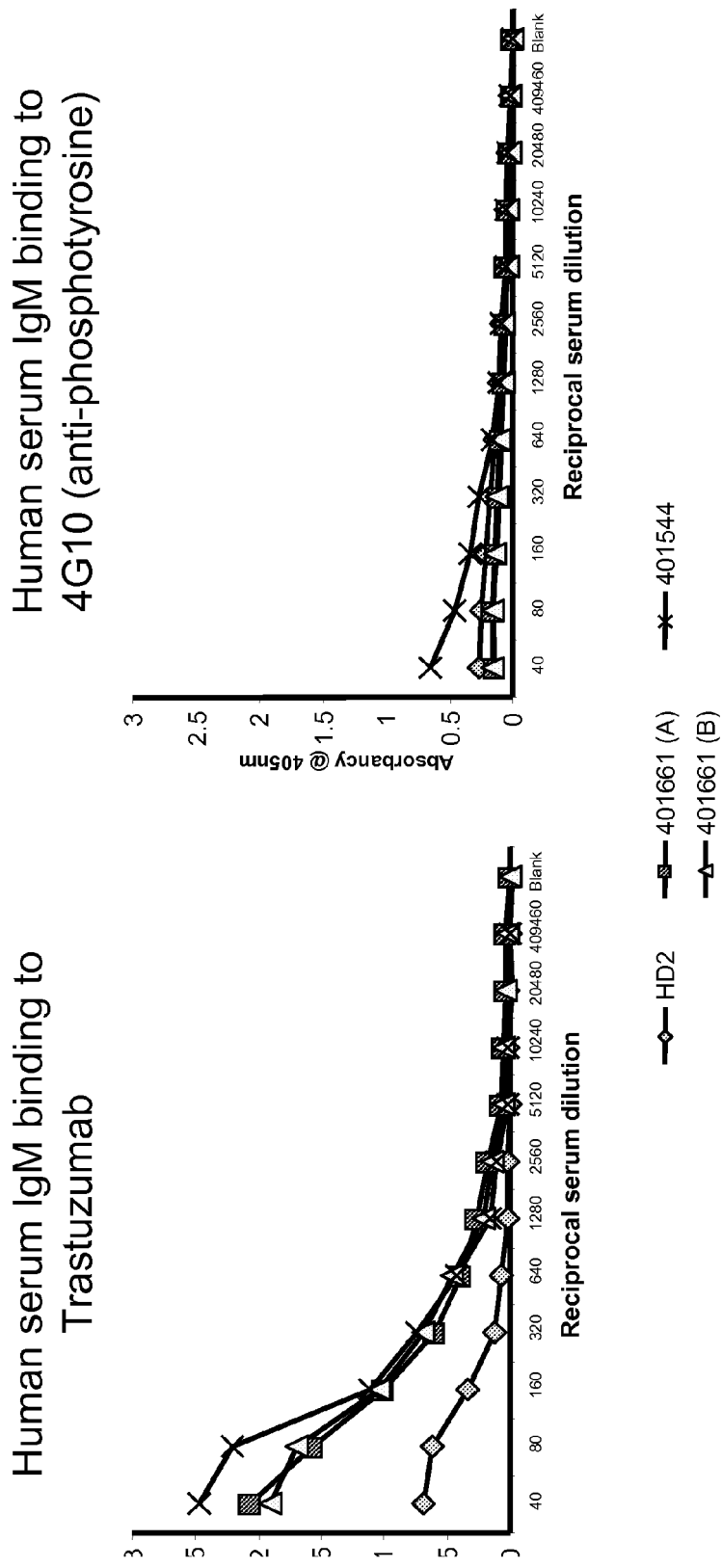
FIG. 2 shows an ELISA for an exemplary Ab2 (an antibody that reacts immunologically with an anti-tumor antigen antibody) (human serum IgM binding activity to trastuzumab and to 4G10).
Figure 3:
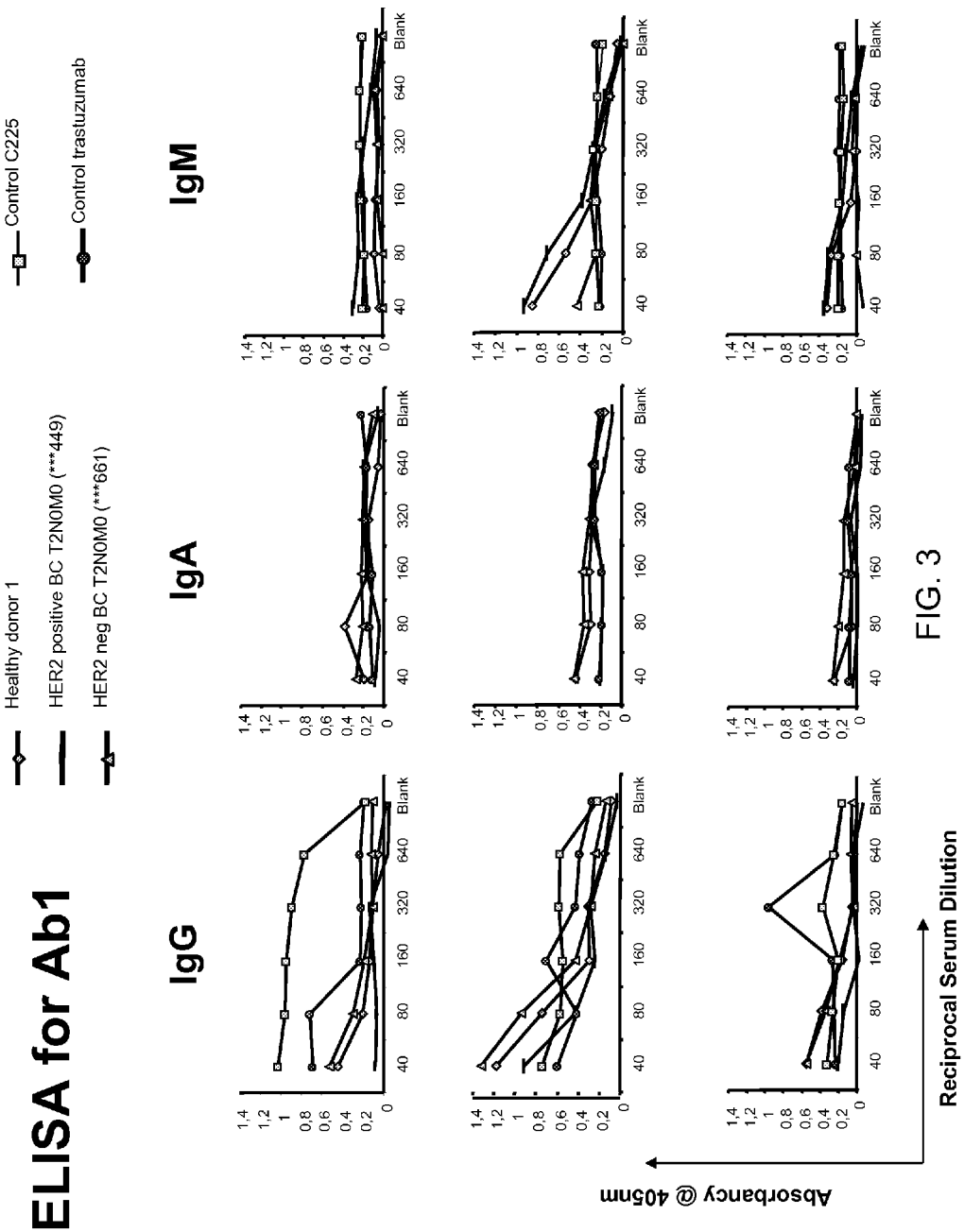
FIG. 3 demonstrates an ELISA for an exemplary Ab1 (an anti-tumor antigen antibody).

FIG. 2 shows an ELISA for Ab2, particularly human serum IgM binding activity to trastuzumab and to 4G10. FIG. 3 demonstrates an ELISA for Ab1. This figure shows a comparative ELISA in which plates were coated with trastuzumab or 4G10 (IgG1 directed to phosphotyrosine), the latter being used as a control. The graphs shows that the patients who had higher titers of Ab2 directed to trastuzumab did not have Ab2 against 4G10. This experiment showed the higher titers were antibody-specific (against trastuzumab).

Thus, in certain aspects of the invention there is an immune network related to cancer immunity and also related to therapeutic antibodies. In further aspects of the invention, the presence of the immune network is beneficial in subjects, such as providing a means to augment that immunity in an effort to reduce the number of, reduce proliferation of, or eradicate malignant cells. In further specific aspects, the observation that HER2-specific antibodies can be identified in some women with HER2 negative breast cancer underlines the possibility of an active immunoselection for HER2 negative variants.

Example 2

Discrimination of Prognosis in AB2 Versus AB1

Figure 4:
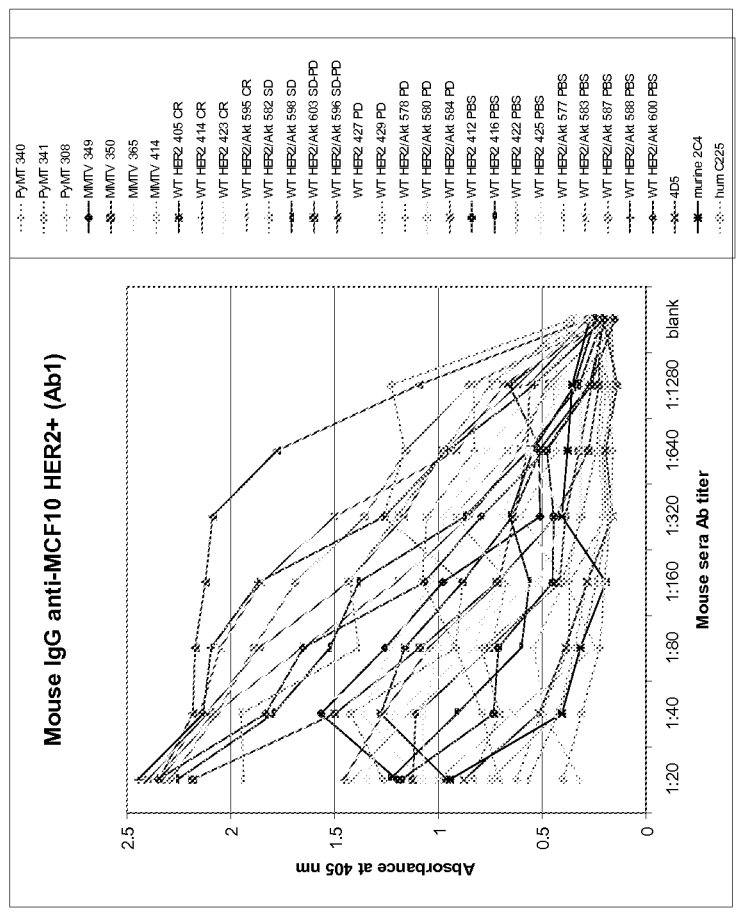
FIG. 4 shows mouse IgG anti-MCF10 HER2+ (Ab1) data.
Figure 5:
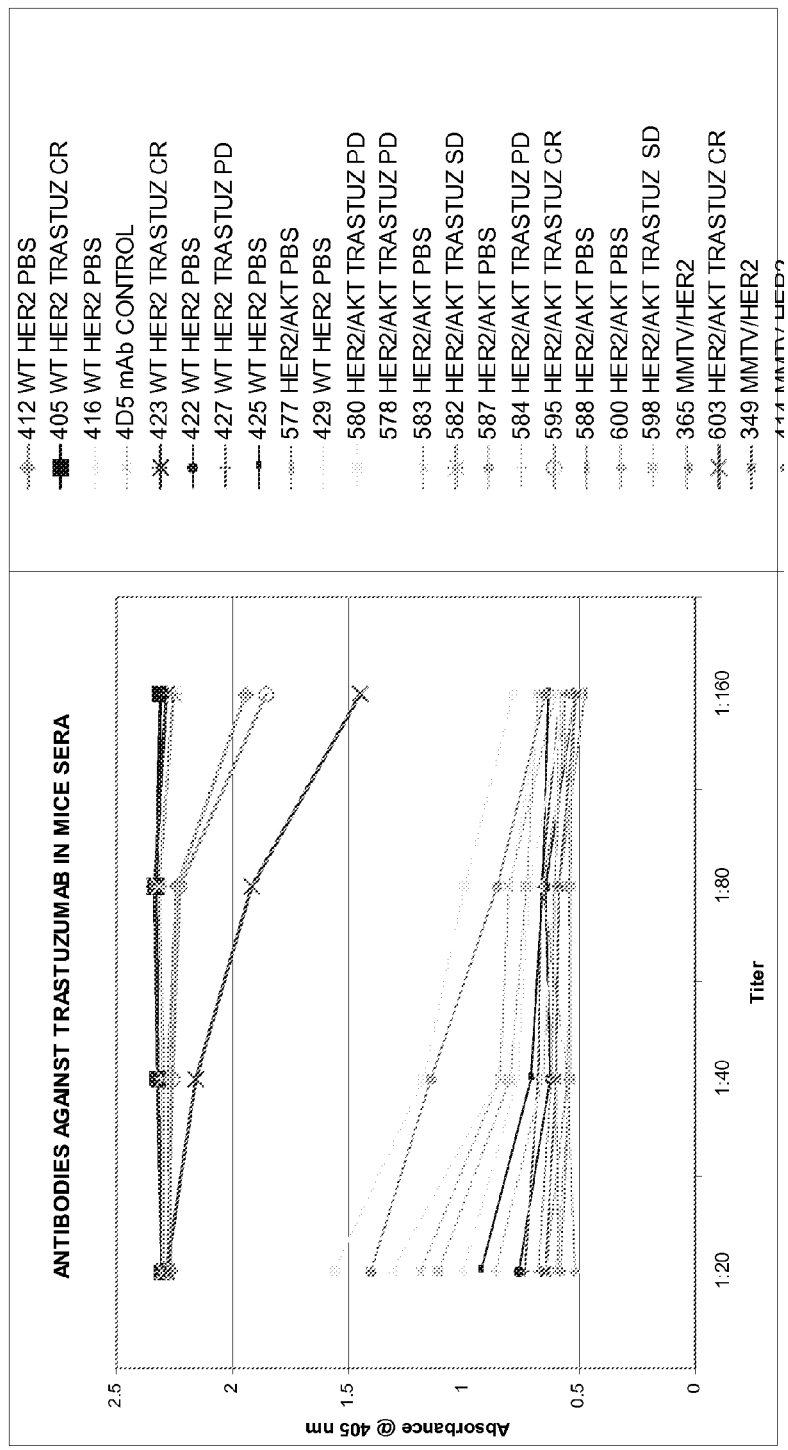
FIG. 5 shows data demonstrating antibodies against trastuzumab in mice sera.

This example concerns the comparison between antibody 1 (the exemplary endogenous anti-HER2) and antibody 2 (the exemplary endogenous anti-anti-HER2). It is noteworthy that Ab1 is not discriminative of prognosis (FIG. 4, which illustrates mouse IgG anti-MCF10 HER2+ (Ab1)), although Ab2 is discriminative of prognosis (FIG. 5, which illustrates antibodies against the exemplary trastuzumab in mice sera). These figures provide data from two independent studies with the serum of almost the same mice. As used herein, CR refers to complete remission; PD refers to progressive disease; SD refers to stable disease; WT refers to wild type (not transgenic); and PyMT refers to Polyoma Middle T transgenic mice that develop mammary gland tumors that are HER2 negative; therefore, they are useful as a negative control.

Example 3

Natural Antibodies Exist Against Other Therapeutic Antibodies Than Trastuzumab

Figure 6:
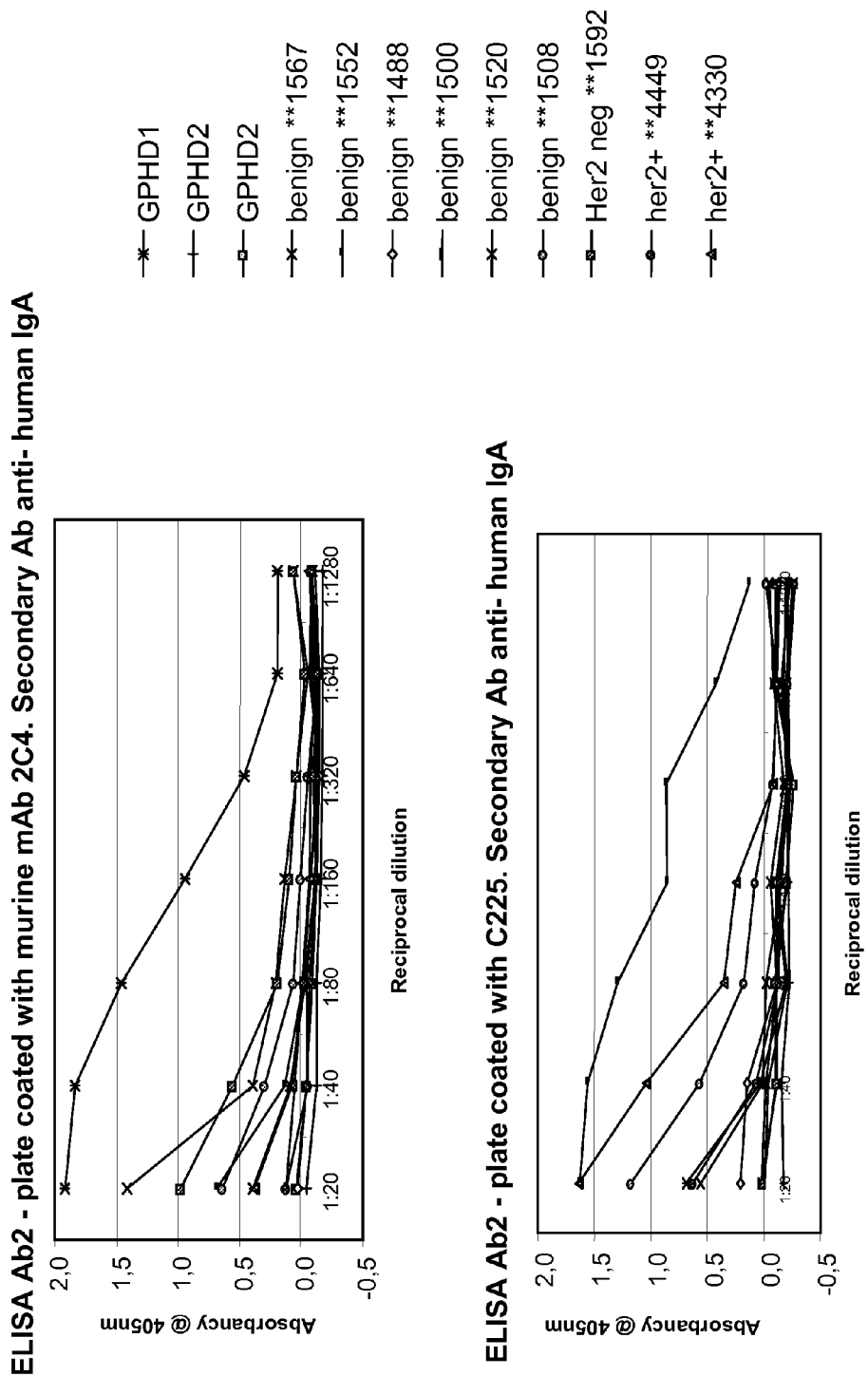
FIG. 6 demonstrates that there are natural antibodies against therapeutic antibodies other than trastuzumab.

The inventors sought to determine whether there are natural Abs against other available therapeutic Abs than trastuzumab. FIG. 6, top half, shows illustration of an ELISA of Ab2, which is a plate coated with murine mAb 2C4, another anti-ERBB2 monoclonal antibody. The secondary antibody utilized was anti-human IgA. In FIG. 6, lower half, there is illustration of an ELISA Ab2, which utilized a plate coated with C225. The secondary antibody utilized was anti-human IgA.

Example 4

Passive Immunotherapy in WT Mice Transplanted with MMTV/HER2 Spontaneous Tumors

In the present Example, the inventors address if MMTV/HER2 mice have any evidence of an immune network present involving HER2 epitopes (they are expected to be tolerant to HER2 epitopes as they are born with HER2 overexpression and develop HER2+ tumors during life). The inventors also address if WT mice transplanted with HER2+ tumors (from MMTV/HER2 mice) have any evidence of an immune network present, in which case they could be employed as a mouse model for further characterization of the immune network.

Twelve experimental mice were utilized for the study, including the following: MMTV/HER2 male mice=3 mice; PyMT mice controls=2 mice; WT transplanted with HER+ tumors PBS treatment group=3 mice; WT transplanted with HER+ tumors Trastuzumab treatment group=4 mice. In the trastuzumab-treated mice, three achieved CR (complete remission) and 1 had PD (progressive disease).

ELISA using 384 well plates coated with different therapeutic Abs and controls may be utilized: 1) Humanized Abs (for example, a) Trastuzumab: humanized mAb; IgG1 kappa; FCgammaRIII; b) C225: humanized mAb; IgG1 kappa; and/or c) Rituxan: humanized mAb; IgG1 kappa; FCgammaRI. Mouse antibodies include the following: a. 4D5: murine Ab IgG1 directed to HER2 (CDRs=trastuzumab); or b. 17B-21A: Anti-HIV mouse Ab as control, for example. Secondary Abs were as follows: 1) Goat anti-mouse IgM peroxidase conjugate for all samples; 2) Goat anti-mouse IgG peroxidase conjugate for humanized Abs; 3) Goat anti-mouse IgA HRP conjugate for mouse Abs (to prevent signal due to the presence of therapeutic Ab constant domains).

Figure 7:
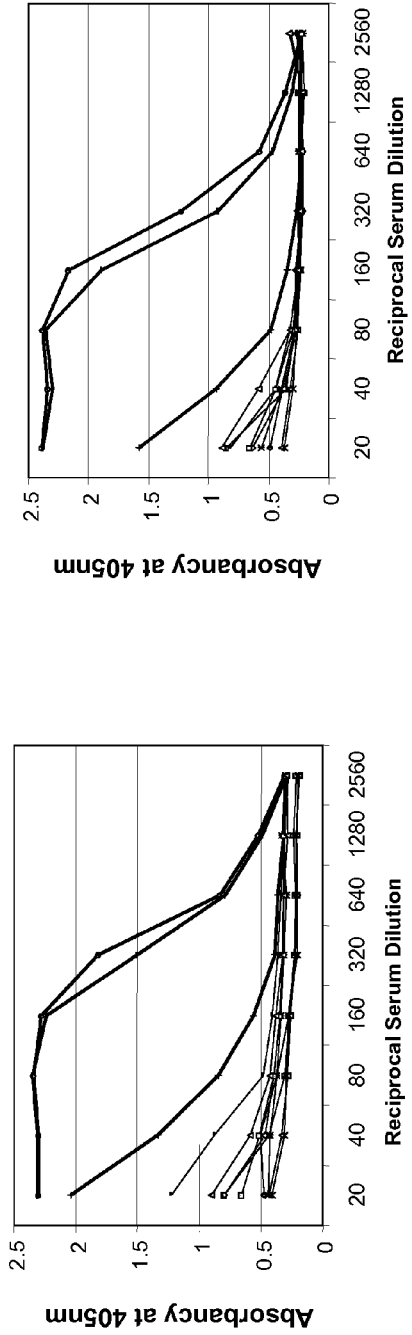
FIG. 7 demonstrates mice serum IgG against therapeutic antibodies.
Figure 7:
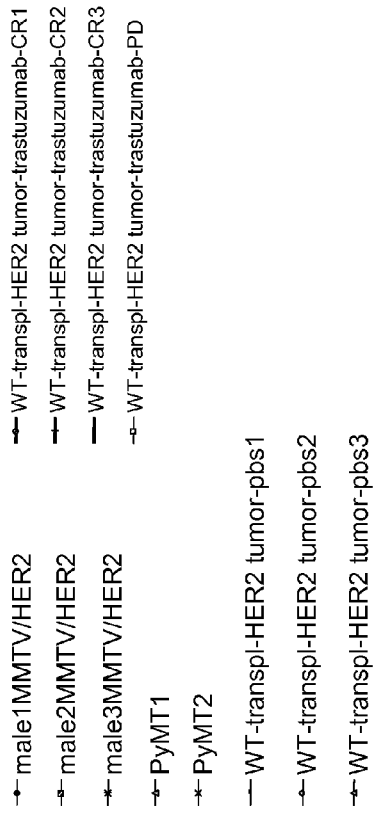
Figure 7:
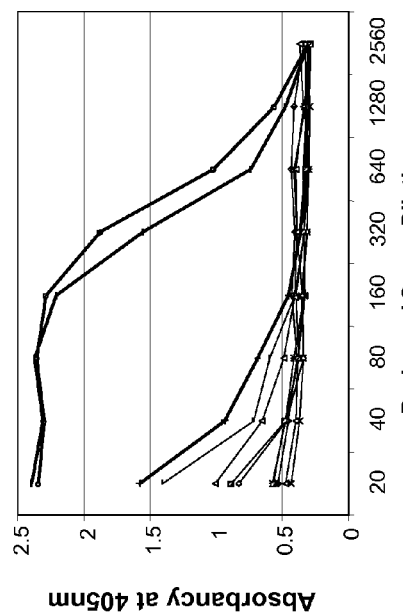

The results were as follows. FIG. 7 shows that from the 12 mice, only 3 had high titers of IgG Abs directed to all trastuzumab, cetuximab and rituximab. In 2 of these mice, Abs were detected in more diluted serum samples. More importantly, the 3 outliners were the 3 complete responders to trastuzumab.

The mouse that received trastuzumab and had PD did not have high concentration of Abs against Trastuzumab. Anti-trastuzumab Abs of this mouse were at the same level as anti-trastuzumab Abs from PyMT mice, for instance. As expected, HER2+ males had low titers of anti-trastuzumab Abs, as they were born with HER2 overexpressed and should be tolerant to it. Not producing Abs to HER2, they will not produce Abs to Ab1 (or to trastuzumab). And PyMT had negative titers of Abs against trastuzumab and cetuximab, as they are not exposed to HER2 (consistent with all other experiments using PyMT serum). Mouse #PBS 1 (WT transplanted with HER2+ tumor treated with PBS) had intermediate titers of trastuzumab, cetuximab and rituximab. (See also FIG. 9). Mouse #2 male MMTV/HER2 mouse and mouse #PBS2 (other WT transplanted with HER2+ tumor treated with PBS) also had absorbance measurements higher than controls, but not sustained with titration of serum sample.

Figure 8:
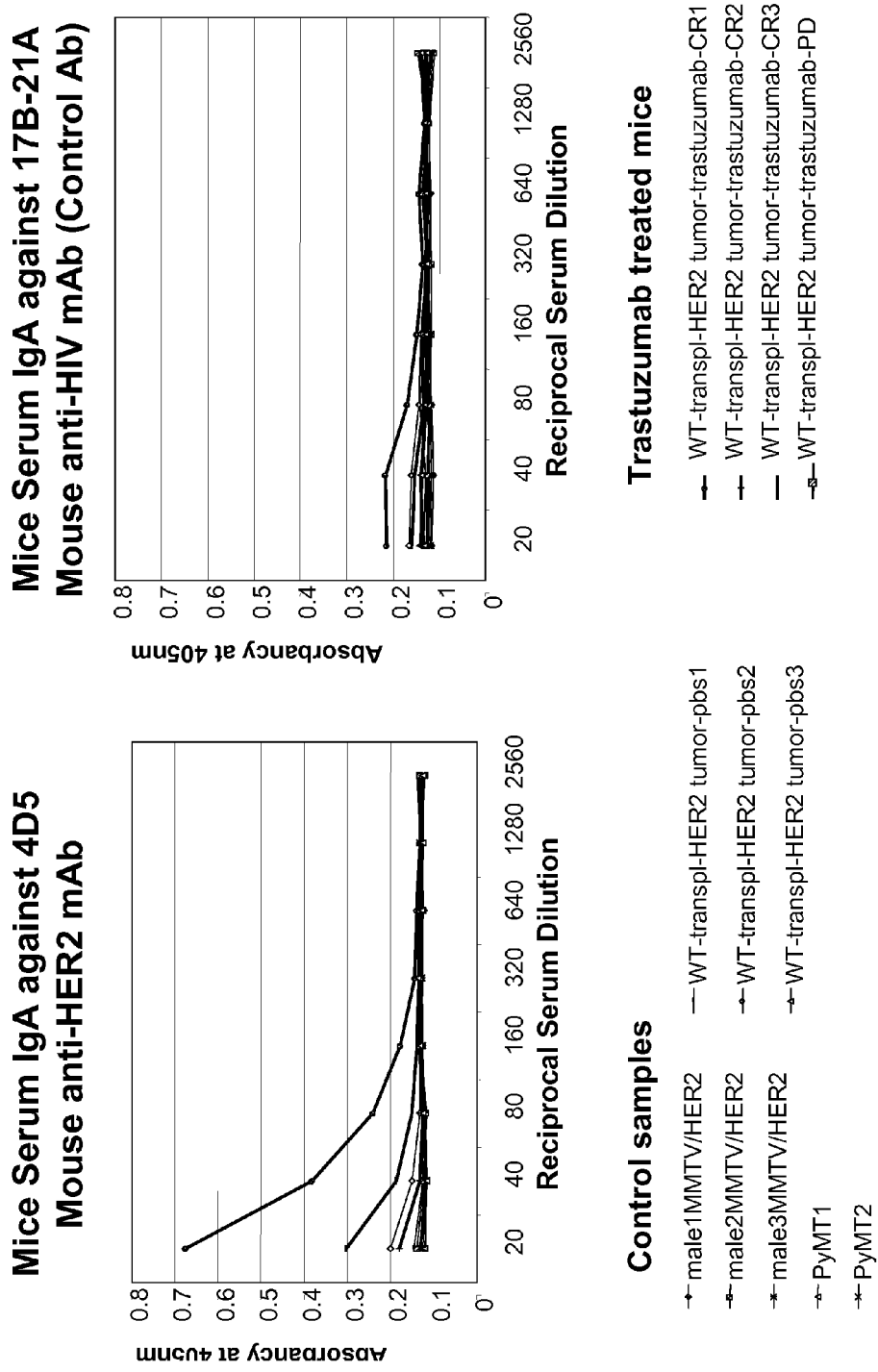
FIG. 8 shows mice serum IgA against therapeutic antibodies.

In FIG. 8, there are two WT mice transplanted with HER2+ tumor treated with trastuzumab that achieved complete remission (CR) had also detectable IgA against 4D5. Response to CDR regions (common in 4D5 and trastuzumab) could account for some of the absorbance read in FIG. 7. This study was not designed to detect mouse IgGs against 4D5.

Figure 9:
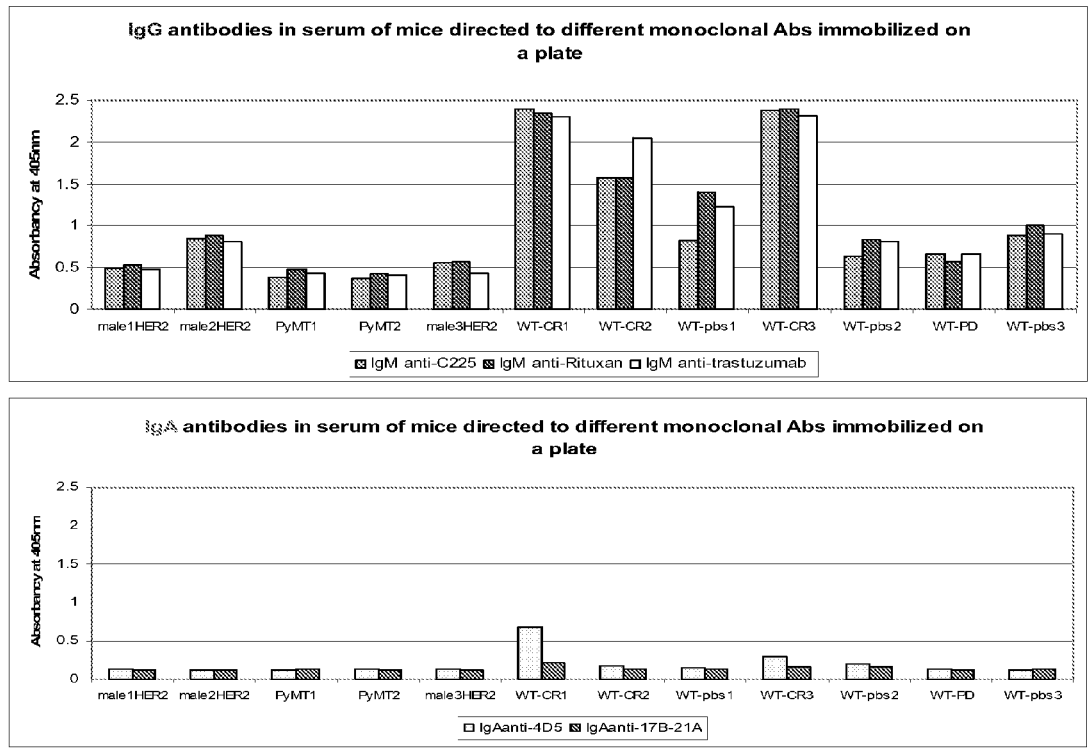
FIG. 9 demonstrates IgM, IgG and IgA titers in mice.

FIG. 9 shows only one of the dilutions of the samples (1:20). Only the CR-treated mice would appear as outliners when taking results from the more diluted samples. Ab class detected in higher titers was IgG. IgM (data not shown) and IgA titers were all very low in the mice samples. The mouse #CR1 had the higher level of IgA anti-4D5 (see also FIG. 8).

Therefore, mice that were able to elicit an immune response to HER2 and to develop an immune network seem to have better prognosis upon trastuzumab treatment. In some aspects of the invention, the presence of anti-trastuzumab, anti-cetuximab and anti-rituximab Abs is due to exposure to treatment with trastuzumab (humanized Ab), whereas in other embodiments the presence of anti-trastuzumab, anti-cetuximab and anti-rituximab Abs is related to the exposure to HER2+ tumors upon transplantation. In particular embodiments of the invention, the presence of these Abs directed to therapeutic Abs is at least a prognostic marker for disease or a predictive marker for response to passive immunotherapy (trastuzumab), for example.

A pattern of positivity of Abs directed to trastuzumab, cetuximab and rituximab was found in mice and in humans, especially in HER2 negative patients (previous findings comparing HER2+ and HER2− early stage non-treated patients). In embodiments related to prognosis, it adds to the idea of immunological clearance of HER2+ cells population in humans, from DCIS to invasive cancer. In other embodiments, this pattern points to response to the framework region that are the same in all humanized Abs tested here. In these embodiments, one should not rely solely on demonstration of responses to the CDR region of therapeutic Abs, as anti-FW responses might be more relevant clinically. In this particular study, 4D5 analysis was not done because the present inventors did not test it for IgG, as it is a mouse Ab. IgA and IgM in this study were all low or negative. The mouse Ab used as a control 17B-21A was also all negative.

Mouse #2 (MMTV/HER2), mouse #8 (WT+HER2+transplant+PBS) and mouse #12 (WT+HER2+transplant+PBS), that have never been treated with trastuzumab had intermediate titers of anti-therapeutic Abs. In specific embodiments of the invention, they would be have a reduction in cancer cell proliferation, if not cured by, trastuzumab if they had the chance to receive the treatment.

The present invention provides a tool to select patients for immunotherapy treatment of cancer. In particular aspects of the invention, patients are selected not only by tumor parameters (HER2 status, for example) but also by humoral and/or cellular immunity parameters, which denote their ability to make use of therapy. In particular embodiments of the invention, such as for breast cancer and for lymphomas, for example, the earlier the stage, the higher the impact measured by response/survival.

In further embodiments, serum from these 12 mice are screened for trastuzumab serum concentration (they stopped treatment more than 4 weeks before euthanasia) with FMAT 8100, using HER2+ transfected MCF-10A cell line, with appropriate non transfected controls. Human serum will also be screened. In additional further embodiments, the present inventors increase trastuzumab treated mice sample and sample size calculation. In more further embodiments, additional mice are employed in more studies, such as some that are HER2+ and/or some that are HER2/Akt+. Here there may be some variation, as some mice had more than one transplant attempt for take and are likely to have molecularly different tumors in terms of sensitivity to trastuzumab, for example. Serum may be utilized from WT transplanted mice that are on observation and that did not develop tumors after more than 2 months observation time, or serum may be utilized from new WT transplanted mice before and after trastuzumab treatment. Spleens may be collected from all responders (mice), such as for generation of hybridomas. In some embodiments, serum is collected before and after trastuzumab and is correlated with response and toxicity data. Earlier stage disease samples may also be characterized, as Ab production should be higher at earlier breast cancer stages. Samples from tumor repositories outside the U.S. may be employed. In further embodiments, studies related to in vitro validation may be performed, such as with a 3D matrigel model, for example for a tumor response with or without anti-trastuzumab Abs and/or utilizing a complement fixation reaction. Analysis of other Abs from available sample may be performed, such as with mass spectrometry and/or B cell FACS, for example.

Example 5

Influence of the Immune Network on Antibody-Based Anti-Cancer Therapy in a Mouse Model Immunity against HER2/Neu (ErbB2) is present in about 30-50% of patients with HER2+ breast cancer. According to the immune network hypothesis, if there is an immune response with antibody (Ab1) production, there will be a regulatory response, with production of another antibody (Ab2) directed to Ab1. Little is known about the presence of endogenous Ab directed to anti-HER2 Abs in patients. The present inventors have detected endogenous anti-anti-HER2 Abs in the serum of patients with HER2+ and HER2− breast cancer before treatment, but rarely in healthy donors. To further characterize the presence of anti-anti-HER2 Abs and their relationship to passive immunotherapy with monoclonal Abs, the present inventors studied wild type (WT) FVB mice transplanted with spontaneous HER2+ mammary transgenic mouse tumors (from MMTV/HER2 or MMTV/HER2× MMTV/AktDD mice).

The following describes exemplary materials and methods: Transgenic tumors were harvested and aliquoted into 1-mm$^3$ aliquots; each aliquot was transplanted with a sterile probe in the s.c. space near the #1 mammary fat pad just above the shoulder of a syngeneic (FVB) non-transgenic female mouse. A total of 28 mice were divided in the following groups: 12 transplanted with HER2 or HER2×Akt tumors and treated with trastuzumab 30 mg/Kg 2×/wk×4 wks; 10 with HER2 or HER2×Akt tumors and treated with PBS; and controls: 4 MMTV/HER2 untreated mice and 2 MMTV/PyMT (Polyoma middle T oncogene) untreated mice. Mice with HER2+ (n=9) and HER2×Akt (n=13) tumors were analyzed together. Tumor was measured by palpation before start of treatment, then weekly until euthanasia, 4 weeks later. Blood was collected by intracardiac puncture, allowed to clot for 60 min, and centrifuged at 1600 G for 10'. Serum was stored at −80° C. until analysis. ELISAs were performed using 384 polystyrene well plates coated with different therapeutic antibodies (Abs): Anti-HER2 (trastuzumab), anti-EGFR (cetuximab), and a murine anti-HER2 Ab (4D5). Non-HER2 directed Abs were used as controls: rituximab and 17B-21A. Secondary Abs: goat anti-mouse IgM peroxidase conjugate for all samples, goat anti-mouse IgG peroxidase conjugate for humanized Abs and goat anti-mouse IgA HRP conjugate for murine Abs.

Figure 10:
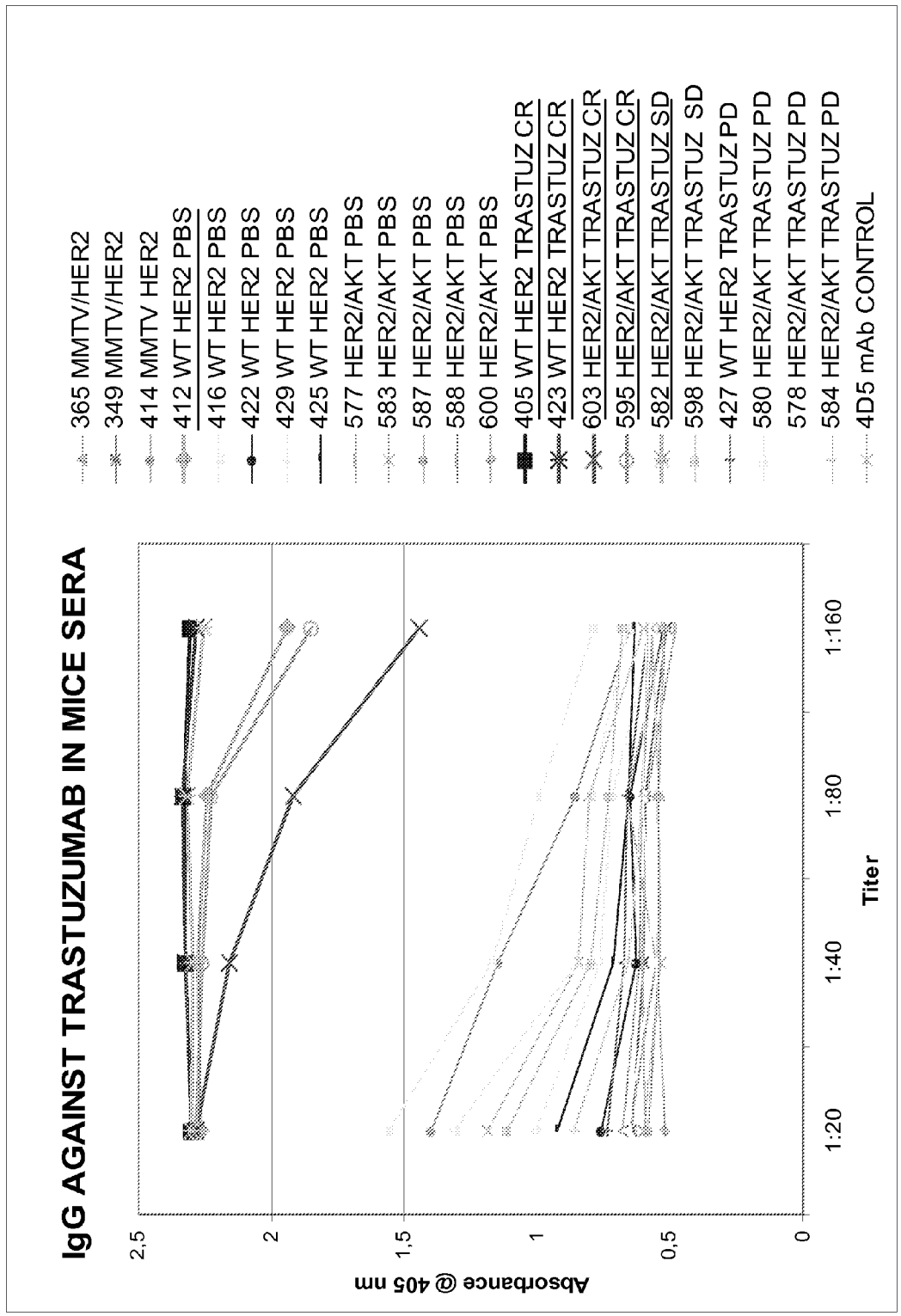
FIG. 10 shows anti-anti-HER2 (anti-trastuzumab) antibodies in mice serum are related to response to treatment with trastuzumab (n=24).

As demonstrated in FIG. 10, in the trastuzumab group (n=10), 4 mice were classified as responders, 2 had stable disease and 4 had progressive disease. Only 6 mice had high titers of IgG Abs directed to trastuzumab (up to 1:160 titer). These 6 mice included all the 4 responders, 1 stable disease and 1 mouse treated with PBS. All the other mice, including those who were resistant to trastuzumab had very low or undetectable anti-anti-HER2 IgG circulating. These Abs were also not detectable in PyMT mice sera. Two of the WT/HER2+ mice that achieved complete remission had also detectable IgA against the mouse HER2 monoclonal 4D5. The same 6 mice had also high titers of Abs against cetuximab and rituximab.

These studies indicate that in syngeneic WT mice transplanted with HER2+ tumors and treated with trastuzumab, complete responses are related to the presence of Abs directed to therapeutic Abs. In specific embodiments, the epitopes in anti-HER2 Abs like trastuzumab are targeted by these endogenous Abs. In some embodiments, the presence of Abs directed to the therapeutic Abs is a prognostic/predictive marker and/or causal to the tumor response to therapy. In specific embodiments, the endogenous Abs (ELISA, flow cytometry and mass spectrometry) are further characterized, and their efficacy is evaluated when used in combination with trastuzumab against HER2+ breast tumors.

Example 6

Confirmation of Antigen-Specific Recognition

In the event that a serum sample comprised multiple antibodies that recognized one or more anti-tumor antigen antibodies, the present inventors distinguished at least some of the antibodies. For example, hybridomas (n=234) were generated from 4 different spleens and kept in culture (for representative samples, see Table 1).

TABLE 1

Antibody Signals for Representative Hybridomas

|  | Hybridoma | Ab type | ELISA signal | Ab class |
|---|---|---|---|---|
| 1 | C1 | anti-anti-EGFR | 0.447 | IgG |
| 2 | D1 | anti-anti-EGFR | 0.438 | IgG |
| 3 | E3 | anti-anti-HER2 | 0.408 | IgG |
| 4 | E11 | anti-anti-HER2 | 0.441 | IgG |
| 5 | H8 | anti-anti-HER2 | 0.404 | IgG |
| 6 | H3 | anti-anti-HER2 | 0.390 | IgG |
| 7 | G6 | anti-anti-HER2 | 0.322 | IgG |
| 8 | E9 | anti-anti-HER2 | 0.332 | IgG |
| 9 | B12 | anti-anti-HER2 | 0.337 | IgG |
| 10 | 4E10 | anti-anti-HER2 | (DOT BLOT) | IgG |
| 11 | H11 | anti-anti-HER2 | (DOT BLOT) | IgM |
| 12 | E12 | anti-anti-HER2 | (DOT BLOT) | IgG |
| 13 | F12 | anti-anti-HER2 | (DOT BLOT) | IgG |
| 14 | E2 | anti-anti-EGFR | (DOT BLOT) | IgG |

After 3 weeks, hybridoma supernatants were screened for anti-anti-HER2 or anti-anti-EGFR Abs using ELISA or Dot Blots. The screening showed that 50 hybridomas were producing Abs that reacted against anti-HER2 (trastuzumab) or anti-EGFR (cetuximab) antibodies. Importantly, hybridomas that reacted to trastuzumab are not the same that reacted to cetuximab. Hybridomas that were positive in ELISA were not the same positive in the dot blot.

Example 7

Identification and Qualification of Candidate Monoclonal Antibodies (MCABS) as "Biomarkers" to Detect Human Antibodies Involved in a Breast Cancer Immune Network Response Study Design.

The study design is organized around and presented in the context of the specific aims. Preliminary data is also presented to demonstrate the feasibility of the proposed experimental design, methods and data analysis described for Aims 1 and 2. Since chemotherapy can potentially alter an Ab-based immune response, only samples from normal and pre-treated breast cancer patients will be used for antibody and assay development.

The inventors designed immunoassays (ELISAs) in which four commercially available therapeutic McAbs—Trastuzumab (Tz), Cetuximab (Cx), Bevacizumab (Bv) and Rituximab (Rx)—are used as Ab1 to assay for the presence of Ab2 in plasma samples from breast cancer patients. Each of these McAbs bind to specific molecules that are over-expressed in certain cancers. Because these McAbs are all humanized IgG1, κ light chain antibodies, they can serve as negative controls for one another to determine Ab2 binding specificity in ELISA.

In the ELISA developed, a secondary peroxidase-conjugated anti-human IgG Fc-specific antibody and an enzyme substrate are used to detect human sample IgG bound to Ab1 (Tz, Cx, By and Rx) coated onto microtiter wells. However, because these Ab1 are humanized IgG, the secondary antibody will also bind to Ab1. To circumvent this problem, pepsin was used to remove the Fc portion of By, Cx, Rx and Tz. Wells of 384-well microtiter plates were then coated with the F(ab')$_2$ fragments of By, Cx, Rx or Tz at a concentration of 75 ng/well then blocked to prevent non-specific binding of human IgG to the plastic. Plasma samples were obtained from a healthy non-cancer patient and from ten breast cancer patients with HER2 positive and negative breast cancer (pre- and post-treatment samples). The test population comprised five patients with stage IV disease, four with stage IIA and one with stage IIB. Nine of the patients were ~61 years old and the remaining patient was 39. Plasma samples were assayed in triplicate for the presence of Ab2 antibodies (IgM, IgG, IgA and IgE) that bound to the F(Ab')$_2$ fragments of Ab1 (Tz, Cx, By or Rx). Anti-human IgG (Fc-specific, reactive with Fc on human sample IgG), IgM (μ-chain specific), IgA (α-chain specific) and IgE (ε-specific) peroxidase conjugates and a peroxidase substrate were used to detect, respectively, human IgG, IgM, IgA and IgE antibodies bound to the Ab1 F(ab')$_2$ fragments.

Figure 11:
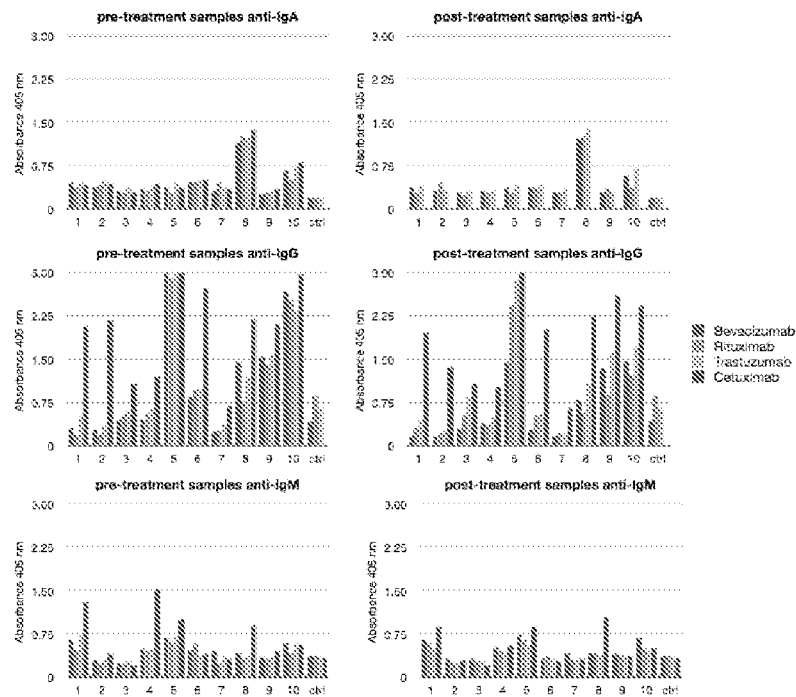
FIG. 11 shows ELISA results for IgG, IgM and IgA antibody binding activity for 10 human breast cancer patient samples and one healthy control on Cx, By, Rx and Tz F(ab')$_2$. Results represent mean of triplicate readings.

By ELISA (FIG. 11), the normal human plasma sample was devoid of antibodies that bound to any of the four Ab1. Several of the pre- and post-treatment plasma samples contained IgM that reacted primarily with Cx. Almost all pre-treatment patient samples contained IgG antibodies that bound to Cx, while less than half of the samples contained IgG that bound to By, Rx or Tz. Samples from patients receiving chemotherapy with or without Tz showed striking differences in IgG and IgA binding activity. When post-treatment samples were compared to pre-treatment samples, the numbers of patients producing IgG binding activity to By increased two-fold while those producing IgA binding activity to By and Tz increased four-fold. Normal and cancer patient plasma samples did not contain IgE that bound to any Ab1.

Figure 12:
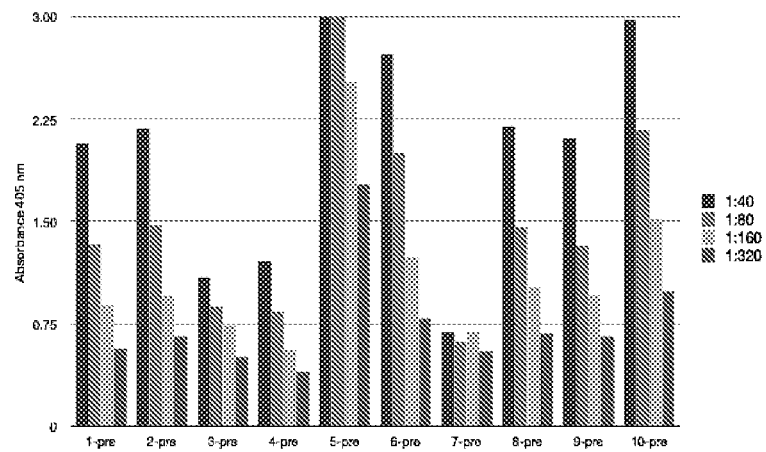
FIG. 12 shows results from an ELISA used to determine IgG anti-Cx levels in 10 pre-treatment breast cancer patient samples diluted 1:40, 80, 160 and 320. Results represent mean of triplicate readings.

ELISA results suggest that some breast cancer patients do make antibodies that bind to Cx, By, Tz and Rx. These results are not unexpected since B-cells, HER2 and VEGF, and Ab2 antibodies made during an immune network response may all be up-regulated during breast cancer. Nearly all pre-treatment breast cancer plasma samples contained IgG anti-Cx F(ab')$_2$ when assayed against Cx in ELISA; however, IgG anti-Cx levels varied from patient to patient (FIG. 12). Cetuximab, unlike By, Rx and Tz, is glycosylated within its heavy chain FW3 region. This glycosylated site contains N-glycolyl-neuraminic acid (NGNA). Antibodies to NGNA have been implicated in human hepatocellular carcinoma (Koda et al., 2003). It is possible that a population of antibodies specific for the NGNA moiety on Cx may exist in breast cancer patients. If so, this would explain why so many of the breast cancer samples contained anti-Cx antibodies. It is also possible that the levels of IgG anti-Cx in breast cancer patients correlate with the stage of the disease. However, it will be necessary to assay a much larger number of normal and breast cancer human samples to determine if results obtained thus far are statistically relevant or biologically significant.

Numerous antibodies are most likely produced to up-regulated or cancer antigens in a breast cancer immune network response. The most efficacious approach to detecting their presence relies on the use of a large phage-displayed (~2.9 billion members) single-chain fragment variable (scFv) antibody library. The inventors have used this library to select for scFv specific for antibodies involved in the breast cancer immune network response. Selected scFv will be developed for use in assays to identify and further characterize the antibody response associated with breast cancer or stage of the disease.

Modifications of previously published protocols (Pope et al., 1996) were used to develop a large (~2.9×10$^9$ or 2.9 billion members) phage-displayed ScFv (single-chain fragment variable) recombinant antibody library. The library has been used to obtain antibodies to different recombinant (Dawling et al., 2001; Du et al., 2005), Akt (Shin et al., 2005), hapten (Davies et al., 2004), peptide (Zhang et al., 2004) and bacterial (Hennig et al., 2004) protein antigens, metals (Edl et al., 2005) and an early breast cancer biomarker (Bradley et al., 2007), with affinities as high as 65 pM. The ScFv are encoded within the pCANTAB5E phagemid vector. The vector contains an ampicillin resistance gene to select for bacterial clones that contain the ScFv-containing phagemid. All ScFv are expressed either as a phage gene 3 fusion protein (for phage display purposes) or as a ~27 kD, soluble E-tagged ScFv. The 11-amino acid E-tag sequence, present on each E-tagged ScFv, is recognized by the Anti-E monoclonal antibody (G.E. Healthcare cat. #27-9412-01). The anti-E monoclonal antibody is used in immunoassays to detect E-tagged ScFv bound to antigens or is used to affinity-purify E-tagged ScFv produced in E. coli.

Figure 13:
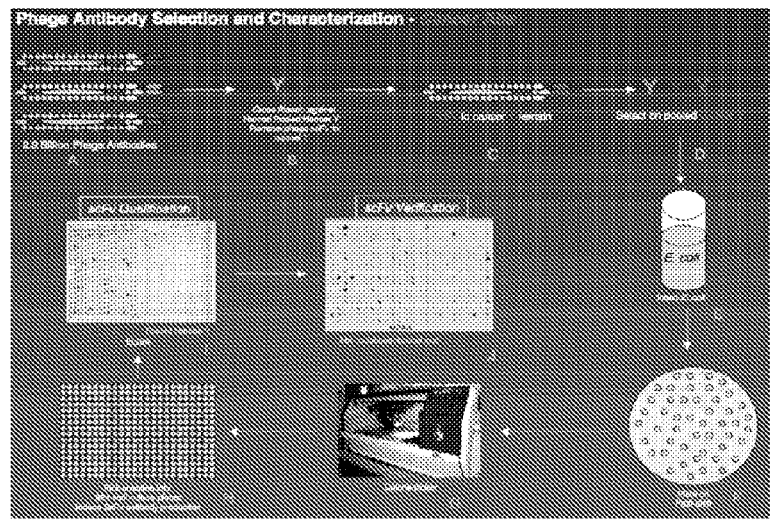
FIGS. 13A-J show the approach used to select for scFv Abs reactive with IgG from lung cancer patients. A similar approach has been initiated to identify scFv reactive with IgG from breast cancer patients.

Phage-displayed antibody selections and antibody characterizations were carried out as shown in FIGS. 13A-J using lung cancer patient samples since adequate sample numbers are currently available. Human IgG was obtained from pooled normal and cancer patient samples. The phage-displayed scFv library (FIG. 13A) was absorbed against normal human IgG (FIG. 13B) to remove scFv reactive with IgG/Ids present in both normal and cancer IgG samples. The cross-absorbed phage library (FIG. 13C) was panned against cancer IgG (FIG. 13D). Phage-displayed scFv bound to cancer IgG was used to infect E. coli (FIG. 13E). Infected E. coli was plated onto agar plates containing ampicillin (FIG. 13F), grown over night and helper phage rescued to produce a breast cancer Ab enriched population of phage-displayed scFv for use in a second round of selection. A second round of cross-absorption on normal and selection on cancer IgG was performed. Bacterial colonies stemming from the second round of selection were picked using a colony-picker (FIG. 13G) to 384 well microtiter plates (FIG. 13H) and induced to express soluble E-tagged scFv for use in assays. Two sets of assays were performed to identify potentially useful scFv. For the ELISA (FIG. 13I) was performed using pooled cancer and normal IgG to assay scFv as part of a qualification step to identify potential cancer IgG-specific scFv. Antibody printing (FIG. 13J) was then performed in which 200 different normal and lung cancer patient samples were spotted singly or in duplicate onto filters and probed with qualified scFv to verify cancer IgG specificity (Mernaugh et al., 2005).

Figure 14:
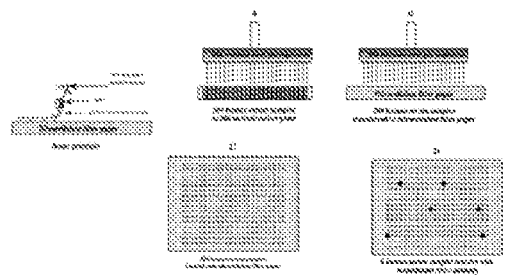
FIG. 14 shows an "antibody printing" assay.
Figure 15:
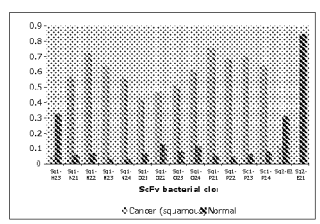
FIG. 15 shows an antibody "qualification" assay.
Figure 16:
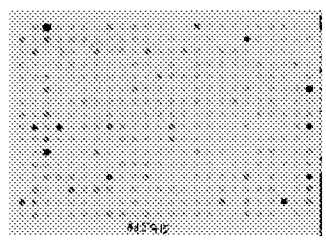
FIG. 16 shows an antibody "verification" assay.
Figure 17:
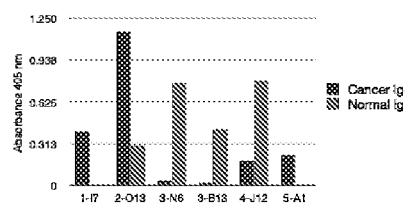
FIG. 17 shows and antibody "discovery" assay.
Figures 1, 18:
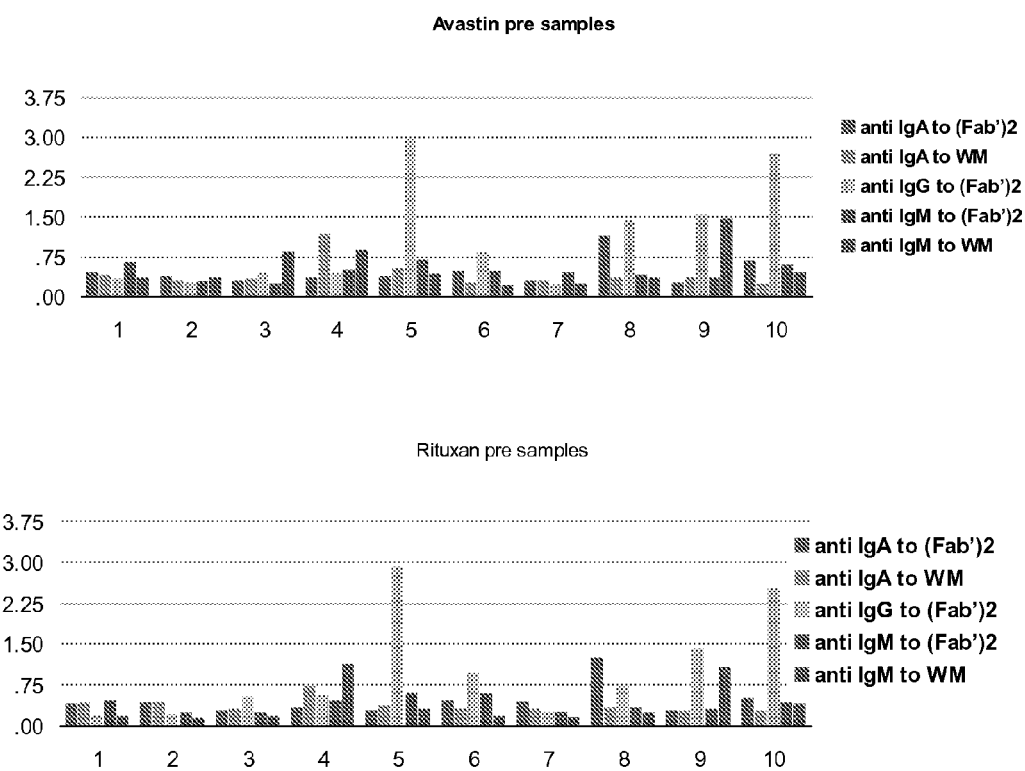
FIGS. 18-25 show IgA and IgM data for untreated patients (designated pre-treatment, FIGS. 18-21) and treated patients (designated post-treatment, FIGS. 22-25). ELISA results were obtained at a different patient serum sample dilution. Dilution 1 represents the ELISA results when patient serum samples were diluted 1:40, Dilution 2 represents ELISA results for patient serum samples diluted 1:80, Dilution 3 represents ELISA results for patient serum samples diluted 1:160, an Dilution 4 represents ELISA results for patient serum samples diluted 1:320. Patient serum samples were assayed against the whole therapeutic antibody molecule (w.m.) or against the Fab'2 fragment of the therapeutic antibody molecule. The Fab'2 fragment of the antibody was digested with pepsin to remove the bottom part (Fc region) of the antibody.
Figures 1, 19:
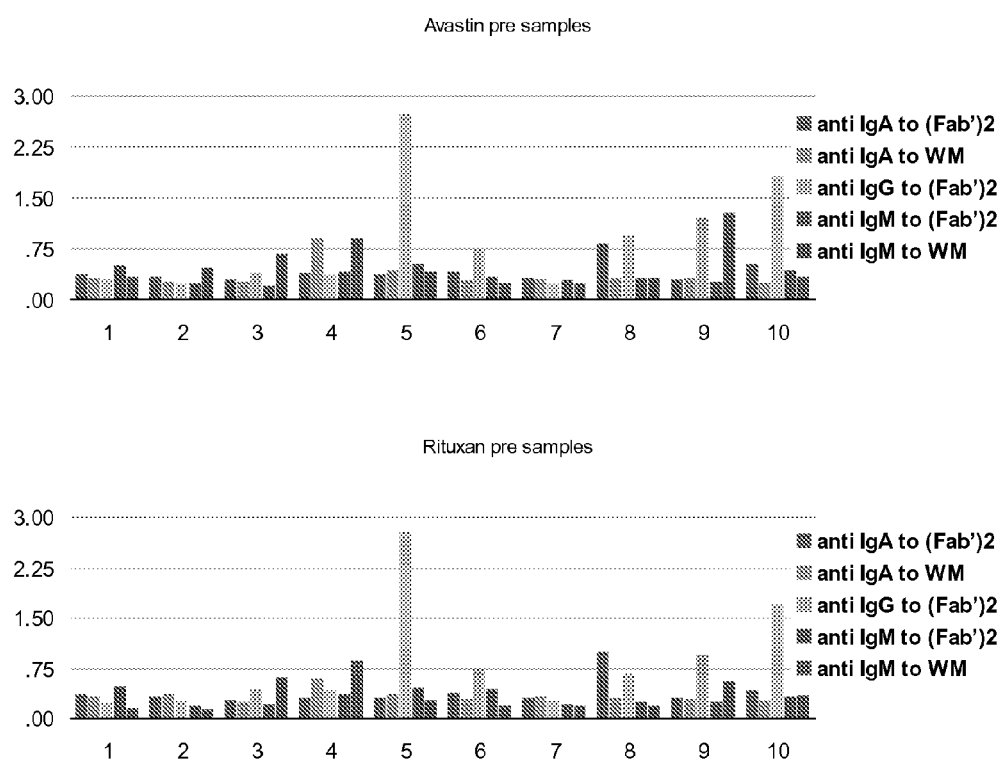
Figures 2, 19:
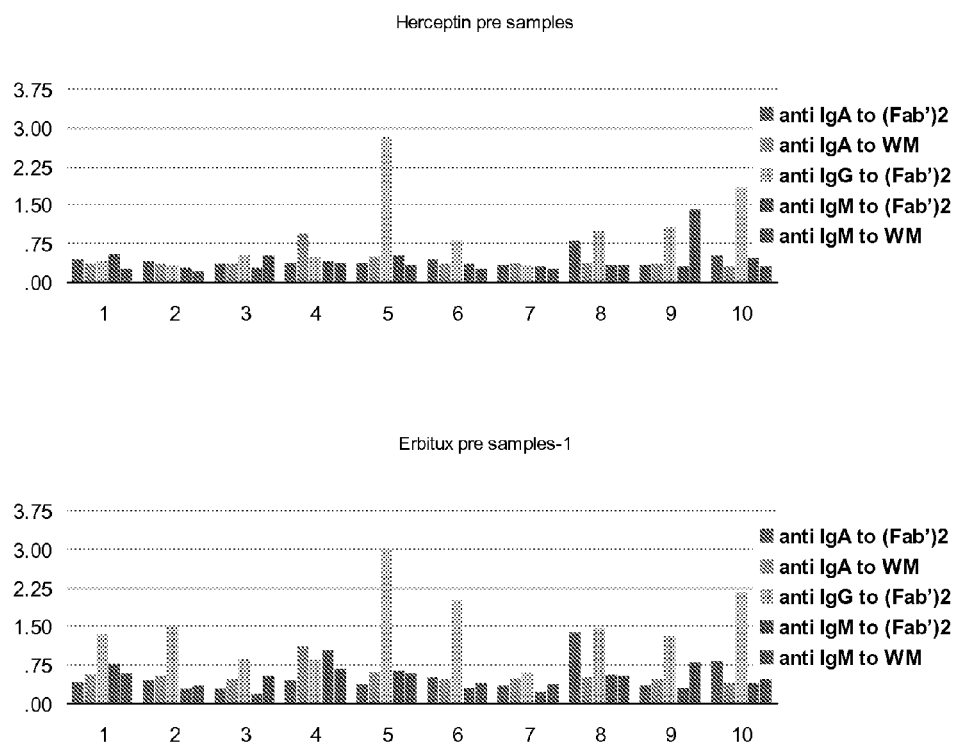
Figures 3, 19:
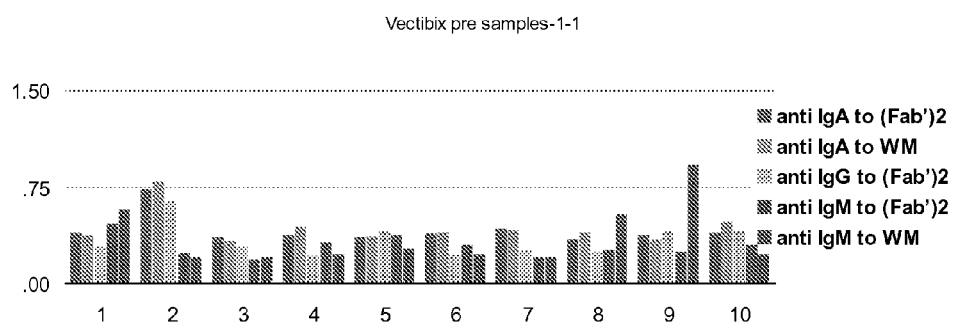
Figures 1, 20:
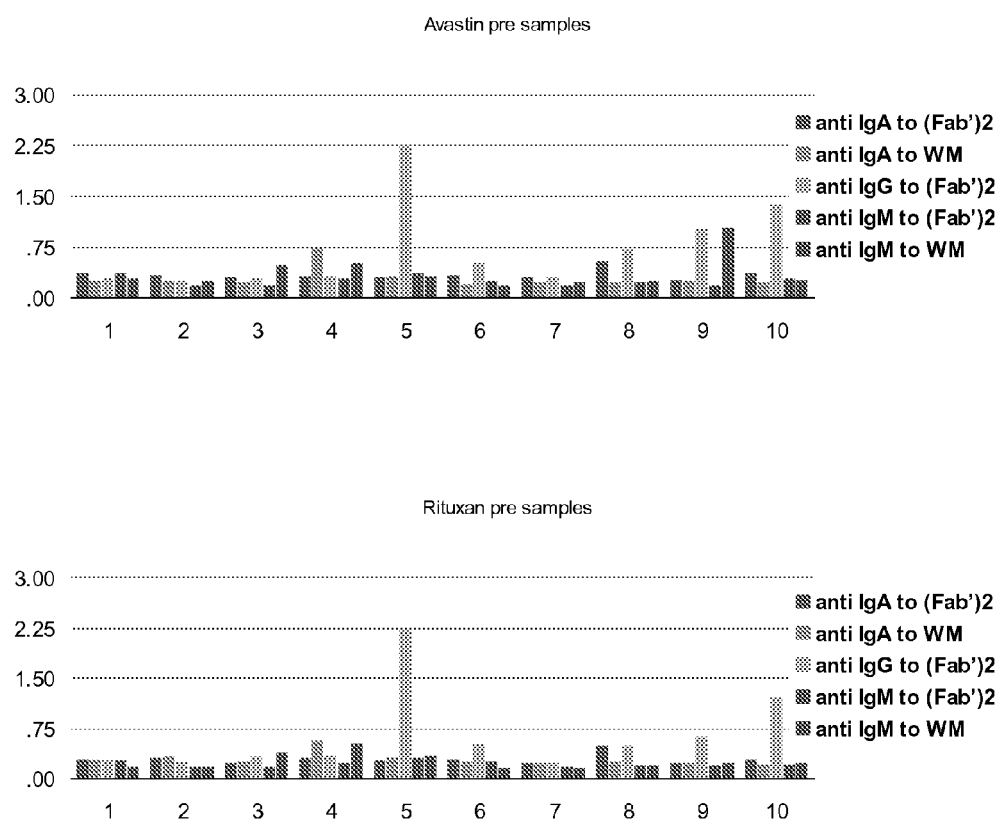
Figures 1, 21:
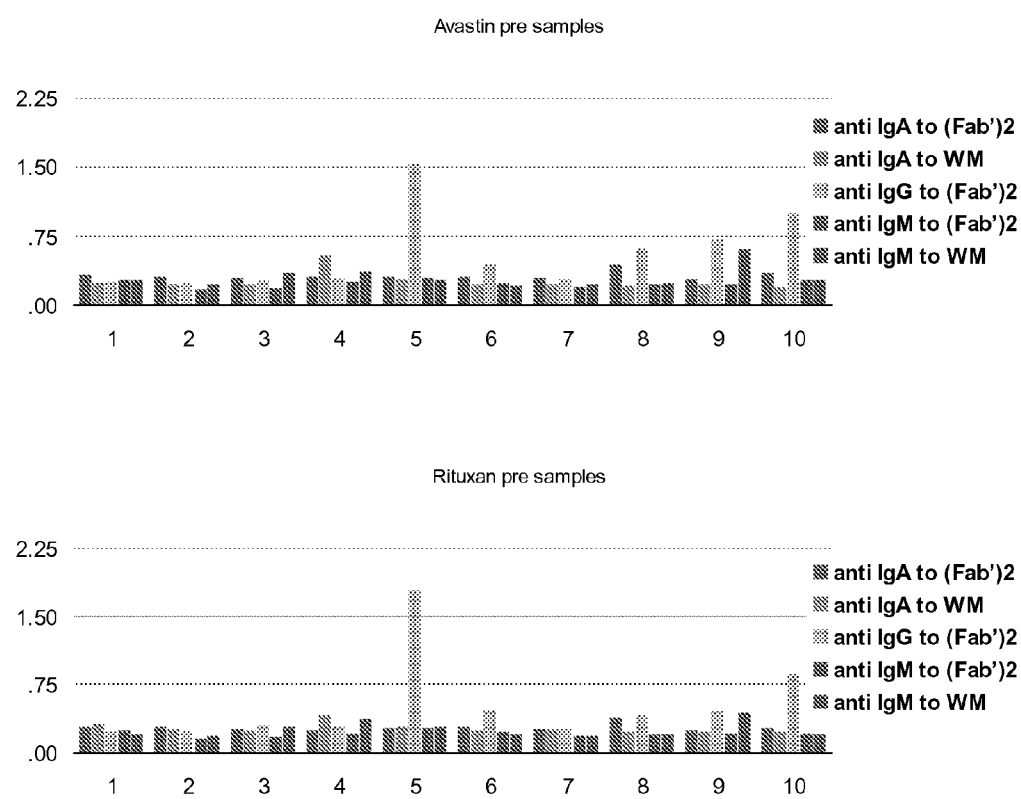
Figures 2, 21:
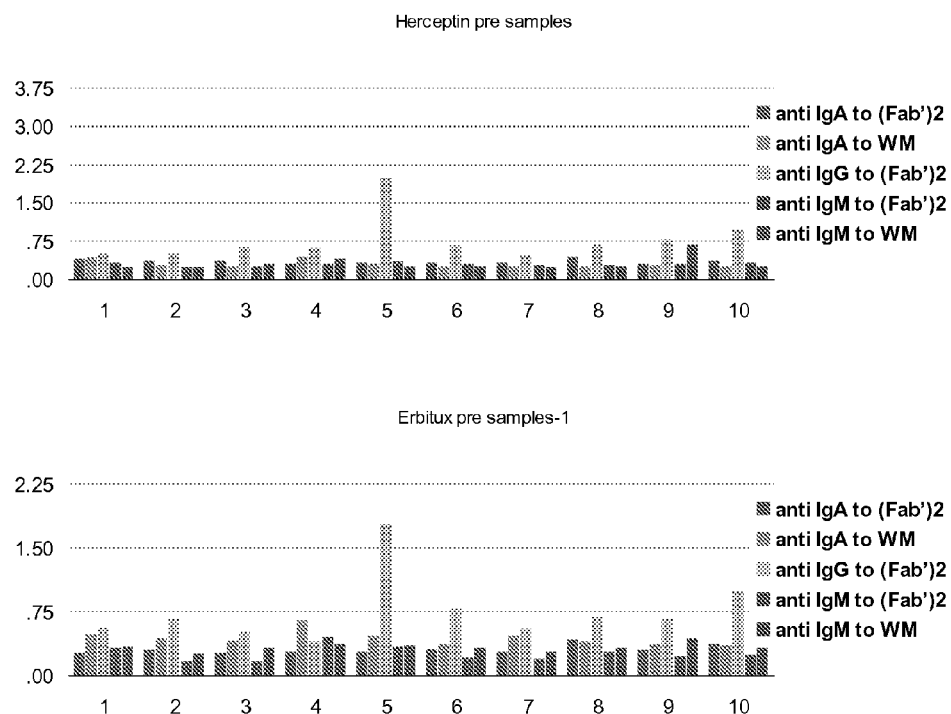
Figures 3, 21:
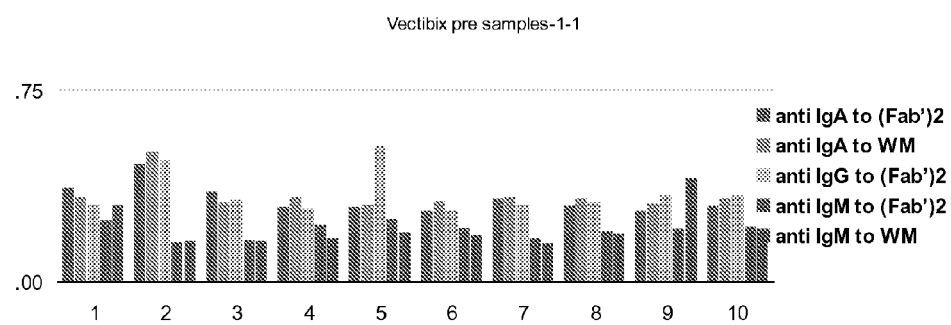
Figures 1, 22:
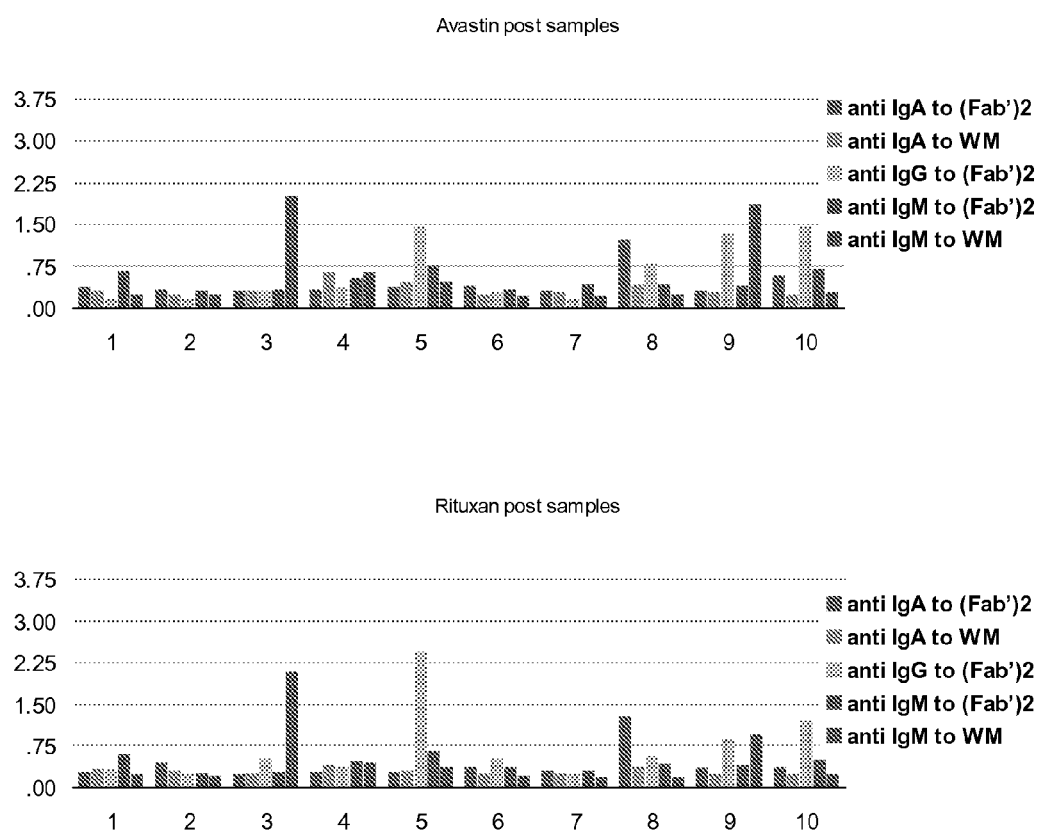
Figures 1, 23:
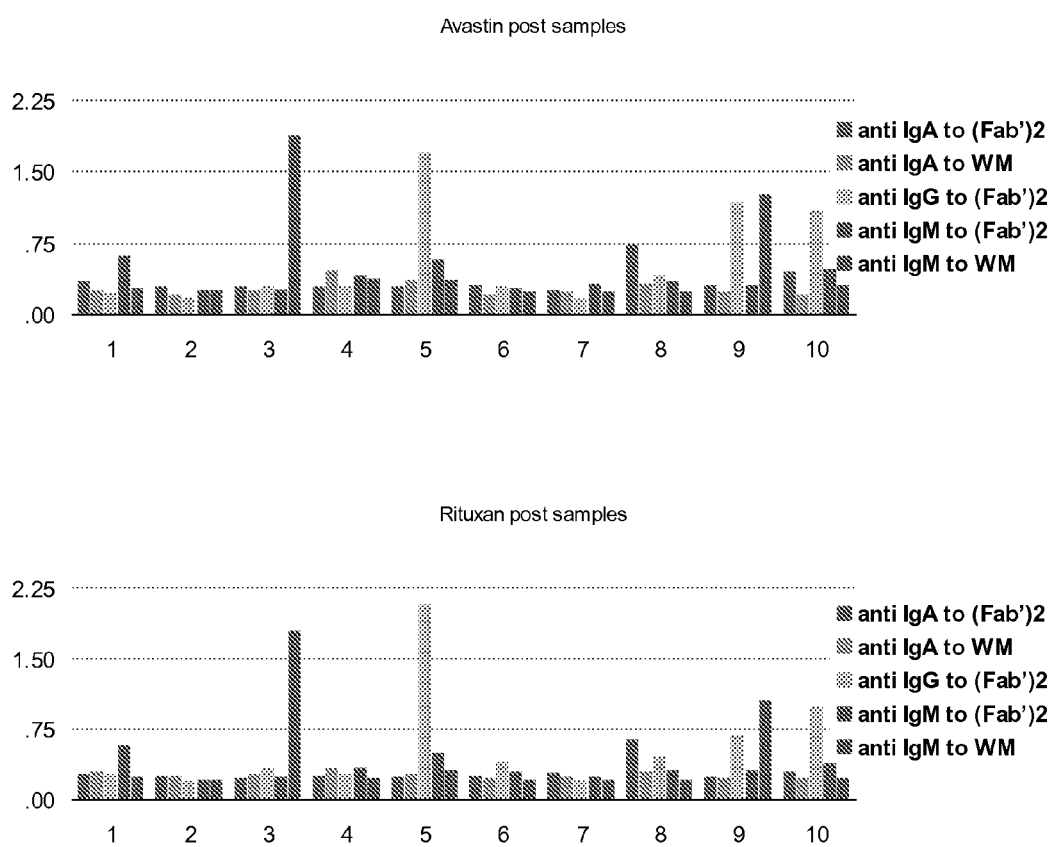
Figures 1, 24:
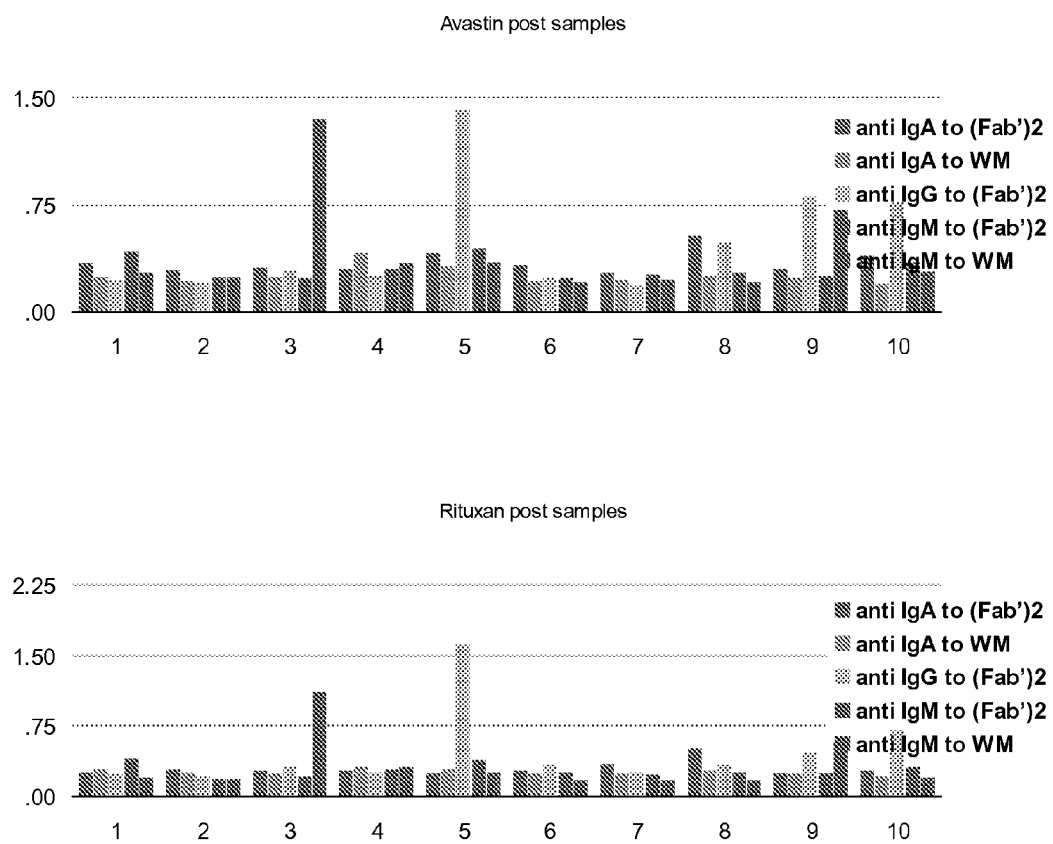
Figures 1, 25:
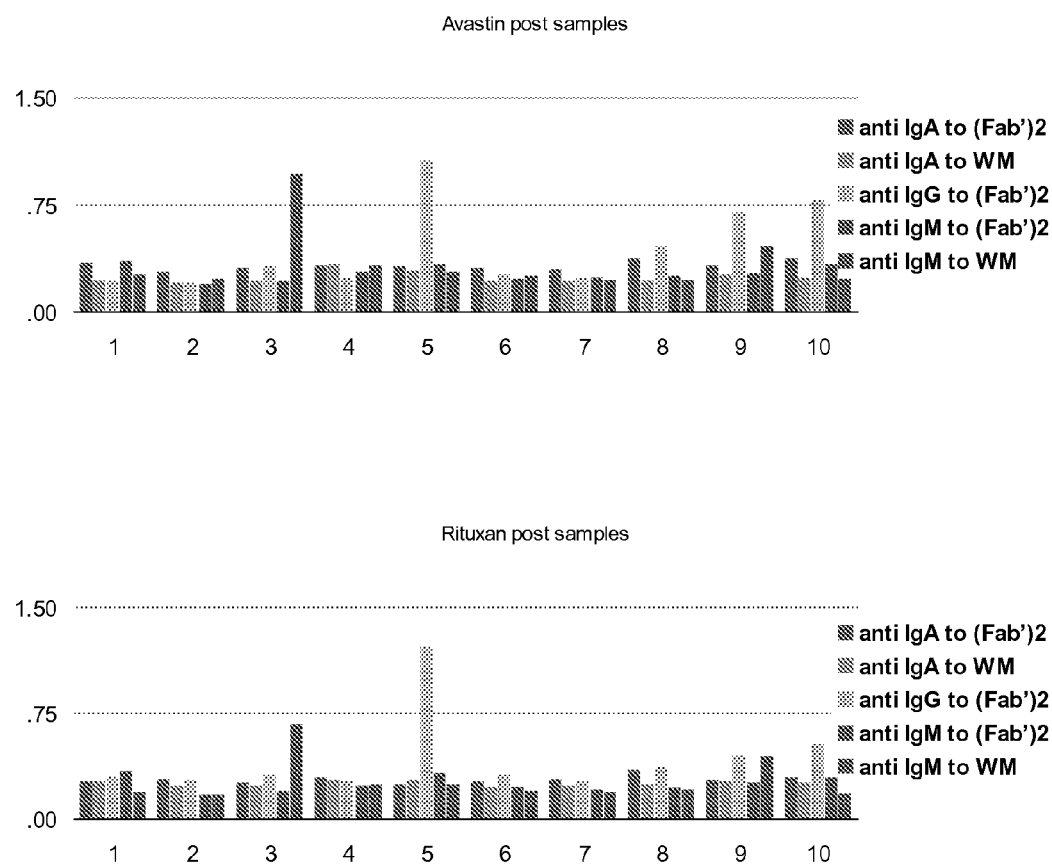
Figures 2, 25:
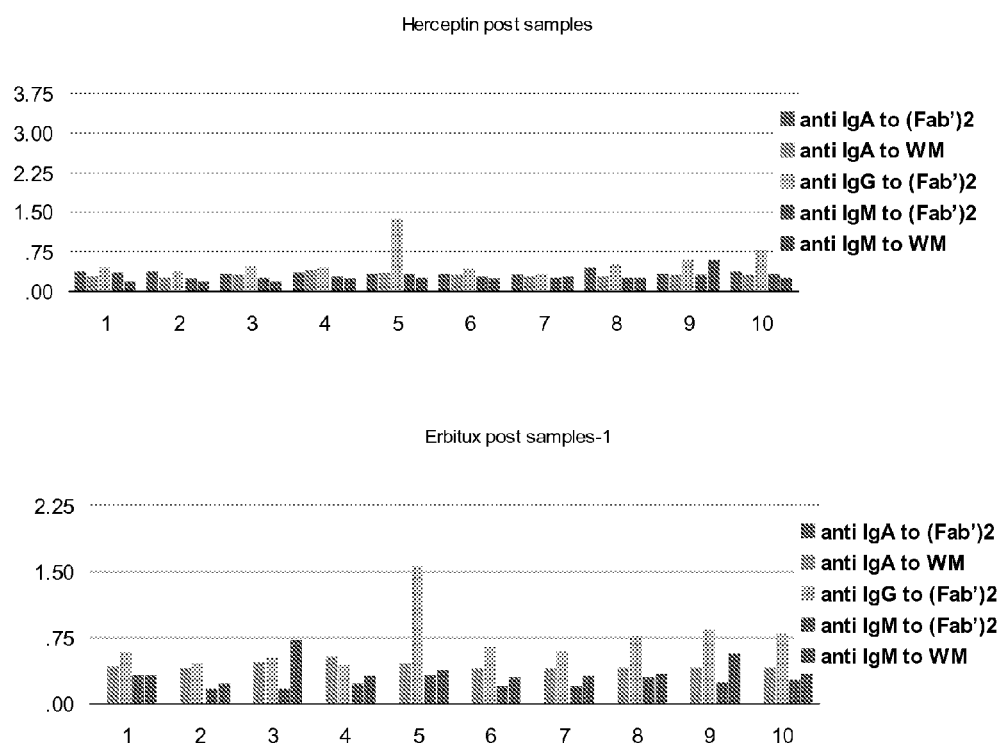
Figures 3, 25:
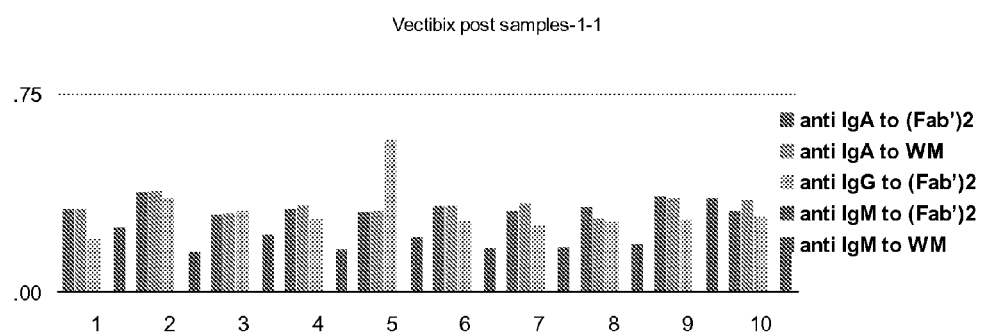

The approach used to perform antibody printing is depicted in FIG. 14. Normal or cancer patient samples are transferred to a 384-well microtiter plate. A 384-well pin replicator is used to transfer samples from 384-well plates to a nitrocellulose filter coated with anti-human IgG Fc-specific Ab to capture IgG present in samples. The filter is washed, probed with an E-tagged scFv, Anti-E tag McAb/peroxidase conjugate and a chemiluminescent peroxidase substrate to produce a visible (black dot) signal on film wherever the scFv bind. ScFv that bind to spotted samples from cancer but not normal patients are retained for use in ELISA. Results for scFv lung cancer IgG ELISA qualification assay and for antibody printing verification assay are presented in FIGS. 15 and 16, respectively. Arrows depict antibody-printing results (dark spots) for an scFv on a stage 4 lung cancer patient sample spotted in duplicate on the filter (FIG. 16). The ELISA results for the discovery phase of the breast cancer project are depicted in FIG. 17 in which scFv were screened against normal human and pooled breast cancer IgG. The scFv designated 1-17, 2-O13 and 5-A1 react primarily with IgG obtained from pooled breast cancer patients.

ELISAs using verified scFv to lung cancer IgG are presently being optimized to enhance the cancer to normal IgG immunoassay signal ratio. Optimized ELISAs will then be validated in assays against more than one thousand normal and lung cancer patient samples accrued at Vanderbilt University to determine scFv and assay suitability for use in detecting lung cancer in humans. A similar approach will be used to develop, qualify and verify scFv and scFv-based ELISAs to detect breast cancer and determine disease stage in humans.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

XI. References

The following references and any others listed herein, to the extent that they provide exemplary procedural or other details supplementary to those set forth herein, are specifically incorporated herein by reference in their entirety.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,938,948
U.S. Pat. No. 5,021,236
U.S. Pat. No. 5,196,066
U.S. Pat. No. 5,399,363
U.S. Pat. No. 5,466,468
U.S. Pat. No. 5,543,158
U.S. Pat. No. 5,641,515
U.S. Pat. No. 6,150,584
U.S. Pat. No. 6,800,738
Abbondanzo et al., *Breast Cancer Res. Treat.*, 16:182(151), 1990.
Allred et al., *Arch. Surg.*, 125(1):107-113, 1990.
Antibodies: A Laboratory Manual, Cold Spring Harbor Laboratory, 1988
Atherton et al., *Biol. of Reproduction*, 32:155-171, 1985.
Bei et al., *Oncogene*, 18(6):1267-1275, 1999.

Berberian et al., *Science,* 261:1588-1591, 1993.
Bird et al., *Science,* 242:423-426, 1988.
Bowie et al., *Science,* 253(5016):164-170, 1991
Bradley et al., *Carcinogenesis,* 28:2184-2192, 2007.
Brown et al. *Immunol. Ser.,* 53:69-82, 1990.
Campbell, In: *Monoclonal Antibody Technology, Laboratory Techniques in Biochemistry and Molecular Biology,* Burden and Von Knippenberg (Eds.), Elseview, Amsterdam, 13:71-74/75-83, 1984.
Cleary et al., *Trends Microbiol.,* 4:131-136, 1994.
Davies et al., *Free Radic. Biol. Med.,* 36:1163-1174, 2004.
Dawling et al., *Cancer Res.,* 61:6716-6722, 2001.
De Jager et al., *Semin. Nucl. Med.,* 23(2):165-179, 1993.
Dholakia et al., *J. Biol. Chem.,* 264:20638-20642, 1989.
Disis et al., Cancer Res., 54(1):16-20, 1994.
Disis et al., *J. Clin. Oncol.,* 15(11):3363-3367, 1997.
Doolittle and Ben-Zeev, *Methods Mol. Biol.,* 109:215-237, 1999.
Du et al., *Arch. Biochem. Biophys.,* 435:125-133, 2005.
Edl et al., *Methods Mol. Biol.,* 303:113-120, 2005.
Gefter et al., *Somatic Cell Genet.,* 3:231-236, 1977.
Goding, In: *Monoclonal Antibodies: Principles and Practice,* 2d ed., Academic Press, Orlando, Fla., pp 60-61, 65-66, 1986.
Gulbis and Galand, *Hum. Pathol.,* 24(12):1271-1285, 1993.
Harlow and Lane, In: *Antibodies: A Laboratory Manual,* Cold Spring Harbor Laboratory, Cold Spring Harbor, N.Y., 346-348, 1988.
Hennig et al., *Infect. Immun.,* 72:3429-3435, 2004.
Jakobovits et al., *Nature,* 362:255-258, 1993.
Jakobovits et al., *Proc. Natl. Acad. Sci. USA,* 90:2551, 1993.
Jones et al., *Nature,* 321:522-525, 1986.
Kang et al., *Science,* 240:1034-1036, 1988.
Khatoon et al., *Ann. of Neurology,* 26:210-219, 1989.
King et al., *J. Biol. Chem.,* 269:10210-10218, 1989.
Koda et al., *Int. J. Clin. Oncol,* 8:317-321, 2003.
Kohler and Milstein, *Eur. J. Immunol.,* 6:511-519, 1976.
Kohler and Milstein, *Nature,* 256:495-497, 1975.
Kohler et al., *Methods Enzymol,* 178:3-35, 1989.
Kozbor, *J. Immunol.,* 133(6):3001-3005, 1984.
Kreier et al., In: *Infection, Resistance and Immunity,* Harper & Row, NY, 1991.
Lenert et al., *Science,* 248:1639-1643, 1990.
McCafferty et al., *Nature,* 348:552-553, 1990.
Mernaugh et al., *J. Immunol. Methods,* 306:115-127, 2005.
Nakamura et al., In: *Handbook of Experimental Immunology* (4th Ed.), Weir et al., (eds). 1:27, Blackwell Scientific Publ., Oxford, 1987.
O'Shannessy et al., *J. Immun. Meth.,* 99:153-161, 1987.
Owens & Haley, *J. Biol. Chem.,* 259:14843-14848, 1987.
Pope et al., In: *Construction and use of antibody gene repertoires,* McCafferty et al. (Eds.), Oxford Univ. Press, Oxford, 1996.
Potter & Haley, *Meth. Enzymol.,* 91:613-633, 1983.
Remington's Pharmaceutical Sciences" 15th Edition, pages 1035-1038 and 1570-1580, 1990.
Remington's Pharmaceutical Sciences, 18th Ed. Mack Printing Company, 1289-1329, 1990.
Riechmann et al., *Nature,* 332(6162):323-327, 1988.
Sasso et al., *J. Immunol.,* 142:2778-2783, 1989.
Shin et al., *Cancer Res.,* 65:2815-2824, 2005.
Shorki et al., *J. Immunol.,* 146:936-940, 1991.
Silvermann et al., *J. Clin. Invest.,* 96:417-426, 1995.
Verhoeyen et al., *Science,* 239:1534-1536, 1988.
Zhang et al., *Biochemistry.,* 43:12575-12584, 2004.

The invention claimed is:

1. A method of determining a response of a subject to an anti-cancer treatment that comprises an anti-tumor antigen antibody, the method comprising:
   (a) detecting, in a sample from said subject, an antibody that reacts immunologically with said anti-tumor antigen antibody, and
   (b) further treating said subject with said anti-tumor antigen antibody when step (a) reveals the presence of an antibody that reacts immunologically with said anti-tumor antigen antibody.

2. The method of claim 1, wherein said antibody that reacts immunologically with said anti-tumor antigen antibody is further defined as detecting an anti-idiotypic antibody that reacts immunologically with the variable region of said anti-tumor antigen antibody, wherein the presence of said anti-idiotypic antibody indicates that the subject will respond to said further treatment.

3. The method of claim 1, wherein the antibody that reacts immunologically with an anti-tumor antigen antibody comprises a polyclonal antibody, a monoclonal antibody, a recombinant ScFv (single chain fragment variable) antibody fragment, Fv, VL or VH fragment, a Fab idiotypic antibody fragment, or an anti-idiotypic antibody fragment.

4. The method of claim 1, wherein said subject has not previously received said treatment.

5. The method of claim 1, wherein said subject has previously received said treatment.

6. The method of claim 1, wherein said tumor antigen comprises HER2, (EGFR) HER1. HER3, HER4, VEGFR, CD20, or EpCAM.

7. The method of claim 1, wherein said anti-tumor antigen antibody comprises trastuzumab, cetuximab, rituximab, bevacizumab, edrecolomab, panitumumab or alemtuzumab.

* * * * *

UNITED STATES PATENT AND TRADEMARK OFFICE
CERTIFICATE OF CORRECTION

PATENT NO. : 8,501,417 B2  
APPLICATION NO. : 12/666566  
DATED : August 6, 2013  
INVENTOR(S) : Paula R. Pohlmann et al.

Page 1 of 1

It is certified that error appears in the above-identified patent and that said Letters Patent is hereby corrected as shown below:

In the claims

In claim 6, column 40, line 45, delete "(EGFR) HER1." and insert -- (EGFR) HER1, -- therefor.

Signed and Sealed this  
Tenth Day of December, 2013

Margaret A. Focarino  
*Commissioner for Patents of the United States Patent and Trademark Office*